US008563026B2

(12) United States Patent
Birge et al.

(10) Patent No.: US 8,563,026 B2
(45) Date of Patent: Oct. 22, 2013

(54) PROTEIN-BASED ARTIFICIAL RETINAS

(75) Inventors: Robert R. Birge, Coventry, CT (US); Megan Nollenberger, Willimantic, CT (US); Matthew Ranaghan, Vernon, CT (US); Daniel J. Sandberg, Willimantic, CT (US); Nicole Wagner, Oxford, MA (US)

(73) Assignee: University of Connecticut, Farmington, CT (US)

( * ) Notice: Subject to any disclaimer, the term of this patent is extended or adjusted under 35 U.S.C. 154(b) by 598 days.

(21) Appl. No.: 12/718,780

(22) Filed: Mar. 5, 2010

(65) Prior Publication Data

US 2010/0226957 A1   Sep. 9, 2010

Related U.S. Application Data

(60) Provisional application No. 61/209,284, filed on Mar. 5, 2009.

(51) Int. Cl.
*A61F 2/14* (2006.01)

(52) U.S. Cl.
USPC ......... 424/427; 427/2.24; 514/20.8; 623/6.63

(58) Field of Classification Search
USPC ......... 424/427; 427/2.24; 514/20.8; 623/6.63
See application file for complete search history.

(56) References Cited

U.S. PATENT DOCUMENTS

| | | | |
|---|---|---|---|
| 5,253,198 A | 10/1993 | Birge et al. | |
| 5,268,862 A | 12/1993 | Rentzepis | |
| 5,559,732 A | 9/1996 | Birge | |
| 7,109,136 B2 | 9/2006 | Senecal et al. | |
| 7,135,261 B2 | 11/2006 | Yamazaki et al. | |
| 7,291,540 B2 | 11/2007 | Mech et al. | |
| 7,939,220 B2 | 5/2011 | Oesterhelt et al. | |
| 2006/0009805 A1 | 1/2006 | Jensen et al. | |
| 2006/0187795 A1 | 8/2006 | Redfield et al. | |
| 2009/0032683 A1* | 2/2009 | Knopf et al. | 250/208.1 |
| 2009/0229669 A1 | 9/2009 | Birge et al. | |
| 2009/0268511 A1 | 10/2009 | Birge | |

FOREIGN PATENT DOCUMENTS

| | | |
|---|---|---|
| CN | 102421462 | 4/2012 |
| EP | 2403549 | 1/2012 |
| WO | WO 2008/141271 A1 | 11/2008 |
| WO | WO-2010102205 A2 | 9/2010 |

OTHER PUBLICATIONS

He et al., Oriented Bacteriorhodopsin/Polycation Multilayers by Electrostatic Layer-by-Layer Assembly, 1998, Langmuir, vol. 14, pp. 1674-1679.*
"NCBI Reference Sequence ZP_01253360", First seen on NCBI on Apr. 7, 2006 documentation in PDF format, Apr. 7, 2006.
"NCBI Reference Sequence ZP_01253360.1", (Downloaded from website on Aug. 10, 2011) First seen on NCBI on Apr. 7, 2006.
U.S. Appl. No. 12/365,289, "Office Action", mailed Feb. 8, 2012.
Baliga, et al., "Genomic and genetic dissection of an archaeal regulon", PNAS, Feb. 27, 2001, vol. 98, No. 5; 2521-2525.
Bard, et al., "Artificial Photosynthesis: Solar Splitting of Water to Hydrogen and Oxygen", Acc. Chem. Res, 1995, 28; 141-145.
Birnboim, "A Rapid Alkaline Extraction Method for the Isolation of Plasmid DNA", Methods in Enzymology, 1983, vol. 100; 243-255.
Bowie, et al., "Deciphering the Message in Protein Sequences: Tolerance to Amino Acid Substitutions", Science, Mar. 16, 1990, 247:1306-1310.
Branden, et al., "Introduction to Protein Structure", Garland Publishing Inc., New York, 1991, 247.
Cline, Steven W. et al., "Transformation methods for halophilic archaebacteria", Can. J. Microbiol., 1989, vol. 35, 148-152.
Crittenden, et al., "Soft lithography based micron-scale electrophoretic patterning of purple membrane", J. Micromech. Microeng., 2005, 15; 1494-1497.
Georgescu, Radu et al., "Saturation Mutagenesis", Methods in Molecular Biology, 2003, vol. 231; 75-83.
Greener, Alan et al., "An Efficient Random Mutagenesis Technique Using an *E. coli* Mutator Strain", Methods in Molecular Biology, 1996, vol. 57; pp. 375-385.
Hillebrecht, et al., "Directed Evolution of Bacteriorhodopsin for Device Applications", Methods in Enzymology, 2004, vol. 388; 333-347.
Hillebrecht, Jason R. , "The Characterization and Optimization of Photoactive Proteins for Performance in Optoelectronic Device Applications", A dissertation; Syracuse University, 2000, 1-179.
Hsu, et al., "Reversal of the surface charge asymmetry in purple membrane due to single amino acid substitutions.", Biophys J. 70(5), May 1996, 2358-2365.
Krebs, Mark P. , "Gene replacement in *Halobacterium halobium* and expression of bacteriorhodopsin mutants", Proc. Natl. Acad. Sci. USA, Mar. 1993, vol. 90, 1987-1991.
Krebs, Mark P. , "Intramembrane Substitutions in Helix D of Bacteriorhodopsin Disrupt the Purple Membrane", J. Mol. Biol., 1997, vol. 267; 172-183.
Peck, Ronald F. et al., "Homologous gene knockout in the archaeon *Halobacterium salinarum* with ura3 as a counterselectable marker", Molecular Microbiology, 2000, 35(3); 667-776.
Pfeiffer, et al., "Site-directed spin-labeling reveals the orientation of the amino acid side-chains in the E-F loop of bacteriorhodopsin", J Mol Biol., vol. 287, Issue 1, Mar. 19, 1999, 163-171.
Schranz, et al., "Oriented Purple Membrane Monolayers Covalently Attached to Gold by Multiple Thiole Linkages Analyzed by Single Molecule Force Spectroscopy", Langmuir, 2007, 23; 11134-11138.
Wan, Lianglu et al., "In vitro evolution of horse heart myoglobin to increase peroxidase activity", Proc. Natl. Acad. Sci. USA, Oct. 1998, vol. 95; 12825-12831.
Wen, Juan et al., "Exploring the allowed sequence space of a membrane protein", Nature Structural Biology, Feb. 1996, vol. 3, No. 2; 141-148.
Whaley, Sandra R. et al., "Selection of peptides with semiconductor binding specificity for directed nanocrystal assembly", Nature, Jun. 8, 2000, vol. 405; 665-668.
Wise, et al., "Optimization of bacteriorhodopsin for bioelectronic devices", Trends in Biotechnology, Sep. 2002, vol. 20, No. 9; 387-394.

(Continued)

*Primary Examiner* — Ali Soroush
(74) *Attorney, Agent, or Firm* — Kilpatrick Townsend & Stockton, LLP

(57) ABSTRACT

Multilayer protein films are provided, which comprise native bacteriorhodopsin and/or specialized bacteriorhodopsin mutants as the photoactive element. Also provided are artificial subretinal and epiretinal implants carrying such bacteriorhodopsin films, as well as methods for making and using the same, for example, to treat retinal diseases and conditions.

14 Claims, 16 Drawing Sheets

(56) References Cited

OTHER PUBLICATIONS

You, L et al., "Directed evolution of subtilis in E in *Bacillus subtilis* to enhance total activity in aqueous dimethylformamide", Protein Engineering, 1994, vol. 9, No. 1; 77-83.

U.S. Appl. No. 12/353,282, "Office Action" mailed Apr. 27, 2012, 14.

Bamann, Christian et al., "Spectral Characteristics of the Photocycle of Channelrhodopsin-2 and Its Implication for Channel Function", J. Mol. Biol. 2008, 375: 686-694.

Berthold, Peter et al., "Channelrhodopsin-1 Initiates Phototaxis and Photophobic Responses in *Chlamydomonas* by Immediate Light-Induced Depolarization", The Plant Cell 2008, vol. 20: 1665-1677.

Bringmann, Andreas et al., "Mammalian Retinal Glial (Müller) Cells Express Large-Conductance $Ca^{2+}$-Activated K+ Channels That Are Modulated by $Mg^2$+ and pH and Activated by Protein Kinase A", GLIA 1997, 19:311-323.

Bromley, Keith M. et al., "Bio-Functional Mesolamellar Nanocomposites Based on Inorganic/Polymer Intercalation in Purple Membrane (Bacteriorhodopsin) Films", Advanced Materials 2007, 19: 2433-2438.

Chen, Zhongping et al., "Bacteriorhodopsin oriented in polyvinyl alcohol films as an erasable optical storage medium", Applied Optics 1991, vol. 30, No. 35: 5188-5196.

Chen, Zhongping et al., "Protein-based artificial retinas", TIBTECH 1993, vol. 11: 292-300.

Douglass, Adam D. et al., "Escape Behavior Elicited by Single, Channelrhodopsin-2-Evoked Spikes in Zebrafish Somatosensory Neurons", Current Biology 2008, 18: 1133-1137.

Enz, Ralf et al., "Expression of the Voltage-Gated Chloride Channel ClC-2 in Rod Bipolar Cells of the Rat Retina", The Journal of Neuroscience 1999, 19(22):9841-9847.

Essen, Lars-Oliver, "Halorhodopsin: light-driven ion pumping made simple?", Current Opinion in Structural Biology 2002, 12:516-522.

Ettaiche, Mohamed et al., "Acid-Sensing Ion Channel 2 is Important for Retinal Function and Protects against Light-Induced Retinal Degeneration", The Journal of Neuroscience 2004, 24(5):1005-1012.

Gillespie, Nathan B. et al., "Characterization of the Branched-Photocycle Intermediates P and Q of Bacteriorhodopsin", J. Phys. Chem 2002, 106:13352-13361.

He, Jin-An et al., "Bacteriorhodopsin Thin Film Assemblies—Immobilization, Properties, and Applications", Advanced Materials 1999, 11, No. 6: 435-446.

He, Jin-An et al., "Oriented Bacteriorhodopsin/Polycation Multilayers by Electrostatic Layer-by-Layer Assembly", Langmuir 1998, 14: 1674-1679.

He, Jin-An et al., "Photoelectric Properties of Oriented Bacteriorhodopsin/Polycation Multilayers by Electrostatic Layer-by-Layer Assembly", J. Phys. Chem. 1998, 102: 7067-7072.

Konnerth, A. et al., "Proton-Induced Transformation of Calcium Channel in Chick Dorsal Root Ganglion Cells", J. Physiol. 1987, 386: 603-633.

Koyama, Koichi et al., "Antibody-Mediated Bacteriorhodopsin Orientation for Molecular Device Architectures", Science 1994, 265: 762-765.

Liu, Yunxiao et al., "Layer-by-Layer assembly of biomacromolecules on poly(ethylene terephthalate) films and fiber fabrics to promote endothelial cell growth", J. Biomed. Mater. Res. 2007, 81A: 692-704.

Liu, Yunxiao et al., "Surface modification of poly(ethylene terephthalate) via hydrolysis and layer-by-layer of chitosan and chondroitin sulfate to construct cytocompatible layer for human endothelial cells", Colloids and Surfaces 2005, 46: 117-126.

Marc, Robert E., "Kainate Activation of Horizontal, Bipolar, Amacrine, and Ganglion Cells in the Rabbit Retina", The Journal of Comparataive Neurology 1999, 407:65-76.

Nagel, Georg et al., "Channelrhodopsin-1: A Light-Gated Proton Channel in Green Algae", Science 2002, vol. 296: 2395-2398.

Nagel, Georg et al., "Channelrhodopsin-2, a directly light-gated cation-selective membrane channel", PNAS 2003, vol. 100(24): 13940-13945.

Paula, Stefan et al., "Roles of Cytoplasmic Arginine and Threonine in Chloride Transport by the Bacteriorhodopsin Mutant D85T", Biophysical Journal 2001, vol. 80: 2386-2395.

Petreanu, Leopoldo et al., "Channelrhodopsin-2-assisted circuit mapping of long-range callosal projections", Nature Neuroscience 2007, vol. 10(5):663-668.

Phaneuf, Matthew D. et al., "Modification of Polyethylene Terephthalate (Dacron) Via Denier Reduction: Effects on Material Tensile Strength, Weight, and Protein Binding Capabilities", Journal of Applied Biomaterials 1995, vol. 6: 289-299.

Sasaki, Jun et al., "Conversion of Bacteriorhodopsin into a Chloride Ion Pump", Science 1995, vol. 269: 73-75.

Theogarajan, Luke S. "Supramolecular Architectures for Neural Prostheses", Doctoral Thesis—Massachusetts Institute of Technology 2007, 1-230.

Varo, G et al., "Photoelectric Signals from Dried Oriented Purple Membranes of *Halobacterium halobium*", Biophys. J. 1983, vol. 43: 47-51.

Verweij, J et al., "Horizontal Cells Feed Back to Cones by Shifting the Cone Calcium-Current Current Activation Range", Vision Res. 1996, vol. 36, No. 24: 3943-3953.

Wyers, Marc C. et al., "In Vivo Assessment of a Novel Dacron Surface with Covalently Bound Recombinant Hirudin", Cardiovascular Pathology 1999, vol. 8, No. 3: 153-159.

Zhang, Yu-He et al., "Real-time Holographic imaging with a bacteriorhodopsin film", Optics Letters 1995, vol. 20, No. 23:2429-2431.

Zrenner, Eberhart "The Subretinal Implant: Can Microphotodiode Arrays Replace Degenerated Retinal Photoreceptors to Restore Vision?", Ophthalmologica 2002, 216(suppl 1):8-20.

U.S. Appl. No. 12/353,282, "Office Action", mailed Aug. 16, 2011.

U.S. Appl. No. 12/365,289, "Office Action", mailed Aug. 9, 2012.

Sanz et al., "Opening the Schiff base moiety of bacteriorhodopsin by mutation of the four extracellular Glu side chains", FEBS Lett., Jul. 30, 1999, 191-5.

International Search Report and Written Opinion, PCT Application No. PCT/US10/26362, mailed Dec. 22, 2010.

Dyukova et al., "Optical and Electrical Characterization of Bacteriorhodopsin Films," Biosystems, 1997, 41:91-98.

Peralvarez et al., "Thr90 is a Key Residue of the Bacteriorhodopsin Proton Pumping Mechanism", FEBS Letters, 2001, 508(3):399-402.

\* cited by examiner

D

D

A

B

SEQUENCE LISTING

<160> NUMBER OF SEQ ID NOS: 2

<210> SEQ ID NO 1
<211> LENGTH: 248
<212> TYPE: PRT
<213> ORGANISM: Halobacterium salinarum

<400> SEQUENCE: 1

```
Glu Ala Gln Ile Thr Gly Arg Pro Glu Trp Ile Trp Leu Ala Leu Gly
1               5                   10                  15

Thr Ala Leu Met Gly Leu Gly Thr Leu Tyr Phe Leu Val Lys Gly Met
            20                  25                  30

Gly Val Ser Asp Pro Asp Ala Lys Lys Phe Tyr Ala Ile Thr Thr Leu
        35                  40                  45

Val Pro Ala Ile Ala Phe Thr Met Tyr Leu Ser Met Leu Leu Gly Tyr
    50                  55                  60

Gly Leu Thr Met Val Pro Phe Gly Gly Glu Gln Asn Pro Ile Tyr Trp
65                  70                  75                  80

Ala Arg Tyr Ala Asp Trp Leu Phe Thr Thr Pro Leu Leu Leu Leu Asp
                85                  90                  95

Leu Ala Leu Leu Val Asp Ala Asp Gln Gly Thr Ile Leu Ala Leu Val
            100                 105                 110

Gly Ala Asp Gly Ile Met Ile Gly Thr Gly Leu Val Gly Thr Leu Ala
        115                 120                 125

Lys Val Tyr Ser Tyr Arg Phe Val Trp Trp Ala Ile Ser Thr Ala Ala
    130                 135                 140

Met Leu Tyr Ile Leu Tyr Val Leu Phe Phe Gly Phe Thr Ser Lys Ala
145                 150                 155                 160

Glu Ser Met Arg Pro Glu Val Ala Ser Thr Phe Lys Val Leu Arg Asn
                165                 170                 175

Val Thr Val Val Leu Trp Ser Ala Tyr Pro Val Val Trp Leu Ile Gly
            180                 185                 190

Ser Glu Gly Ala Gly Ile Val Pro Leu Asn Ile Glu Thr Leu Leu Phe
        195                 200                 205

Met Val Leu Asp Val Ser Ala Lys Val Gly Phe Gly Leu Ile Leu Leu
    210                 215                 220

Arg Ser Arg Ala Ile Phe Gly Glu Ala Glu Ala Pro Glu Pro Ser Ala
225                 230                 235                 240

Asp Gly Ala Ala Ala Thr Ser Asp
                245
```

<210> SEQ ID NO 2
<211> LENGTH: 262
<212> TYPE: PRT
<213> ORGANISM: Halobacterium salinarum

<400> SEQUENCE: 2

```
Met Leu Glu Leu Leu Pro Thr Ala Val Glu Gly Val Ser Gln Ala Gln
1               5                   10                  15
```

-continued

```
Ile Thr Gly Arg Pro Glu Trp Ile Trp Leu Ala Leu Gly Thr Ala Leu
            20                  25                  30

Met Gly Leu Gly Thr Leu Tyr Phe Leu Val Lys Gly Met Gly Val Ser
            35                  40                  45

Asp Pro Asp Ala Lys Lys Phe Tyr Ala Ile Thr Thr Leu Val Pro Ala
    50                  55                  60

Ile Ala Phe Thr Met Tyr Leu Ser Met Leu Leu Gly Tyr Gly Leu Thr
65                  70                  75                  80

Met Val Pro Phe Gly Gly Glu Gln Asn Pro Ile Tyr Trp Ala Arg Tyr
                85                  90                  95

Ala Asp Trp Leu Phe Thr Thr Pro Leu Leu Leu Leu Asp Leu Ala Leu
            100                 105                 110

Leu Val Asp Ala Asp Gln Gly Thr Ile Leu Ala Leu Val Gly Ala Asp
            115                 120                 125

Gly Ile Met Ile Gly Thr Gly Leu Val Gly Ala Leu Thr Lys Val Tyr
    130                 135                 140

Ser Tyr Arg Phe Val Trp Trp Ala Ile Ser Thr Ala Ala Met Leu Tyr
145                 150                 155                 160

Ile Leu Tyr Val Leu Phe Phe Gly Phe Thr Ser Lys Ala Glu Ser Met
            165                 170                 175

Arg Pro Glu Val Ala Ser Thr Phe Lys Val Leu Arg Asn Val Thr Val
            180                 185                 190

Val Leu Trp Ser Ala Tyr Pro Val Val Trp Leu Ile Gly Ser Glu Gly
            195                 200                 205

Ala Gly Ile Val Pro Leu Asn Ile Glu Thr Leu Leu Phe Met Val Leu
    210                 215                 220

Asp Val Ser Ala Lys Val Gly Phe Gly Leu Ile Leu Leu Arg Ser Arg
225                 230                 235                 240

Ala Ile Phe Gly Glu Ala Glu Ala Pro Glu Pro Ser Ala Gly Asp Gly
            245                 250                 255

Ala Ala Ala Thr Ser Asp
            260
```

PROTEIN-BASED ARTIFICIAL RETINAS

PRIOR RELATED APPLICATION

The present application claims the benefit of priority to U.S. Provisional Application No. 61/209,284 filed Mar. 5, 2009, which is hereby incorporated by reference in its entirety.

STATEMENT REGARDING FEDERALLY SPONSORED RESEARCH

The research leading to this application was funded in part with United States government support under National Institutes of Health (NIH) Grant No. GM-34548, National Science Foundation (NSF) Grant No. CCF-0432151, and Defense Advanced Research Projects Agency (DARPA) Grant No. HR0011-05-1-0027. Accordingly, the United States government may have certain rights in the application.

FIELD

The present application relates to artificial retinal implants carrying a protein film comprising a native bacteriorhodopsin protein, one or more specialized bacteriorhodopsin mutants, or a combination thereof as the photoactive element, and methods for making and using the same, for example, to treat retinal disease.

BACKGROUND

The retina is a multilayered tissue that lines the concave (inner) surface of the back of the eye. Photoreceptor cells within the retina are activated by light that enters the eye and convert the light signals into electrochemical signals that are conveyed to retinal neurons. The retinal neurons, in turn, relay the signals to the visual centers of the brain via the optic nerve, thereby allowing the brain to perceive visual images. Photoreceptor cells are broadly categorized as rod cells and cone cells (named for their shape). Whereas cone cells contain photopigments that are necessary for color vision, rod cells contain a photopigment, rhodopsin, that is highly sensitive to light and thus allows vision under dim light conditions (e.g., night). A rod cell is sensitive enough to become activated by a single photon of light, whereas a cone cell requires tens to hundreds of photons to become activated.

Rhodopsin, the photoreceptive pigment of rod cells, undergoes a conformational change when activated by a photon of light. Rhodopsin consists of a seven-pass transmembrane protein called opsin that is covalently bound to a prosthetic group called retinal, a derivative of vitamin A. Non-activated retinal exists in the 11-cis form, whereas stimulation by light induces a conformational change to the all-trans form. The conformational change in retinal induces a corresponding conformational change in the covalently bound opsin polypeptide, thereby triggering a second messenger cascade within the photoreceptor cell that results in the transmission of signals to the appropriate retinal neurons. These signals are transmitted along the optic nerve to the visual centers of the brain, which allows the brain to process the visual input and perceive a visual image.

Various diseases and conditions that destroy photoreceptor cells of the retina cause partial or full vision loss. Two major diseases of the retina are age-related macular degeneration (AMD) and retinitis pigmentosa (RP). As the leading cause of vision loss and blindness in older adults, AMD causes both rod and cone photoreceptor cells, located within the macula at the center of the retina, to deteriorate. Furthermore, AMD affects central vision and thus causes difficulty with reading, driving, and other tasks that require high-contrast vision.

The latter disease, RP, is an inherited condition in which the rod photoreceptor cells degenerate, thereby causing vision loss and blindness. The loss of rod cells impairs the ability to see in dim light and gradually reduces peripheral vision until the patient suffers from tunnel vision and, ultimately, blindness.

To date, a number of artificial retina prototypes have been investigated for the treatment of such retinal diseases and conditions, but each has distinct disadvantages. One of the more promising designs, a subretinal implant from Optobionics, employs a silicon diode material to generate electrical stimulation upon light activation. The silicon diode photoreceptor, however, only generates a sufficient current when intense light is used as stimulation and provides only dim vision in the brightest settings. An alternative design is an epiretinal implant designed by researchers at the University of Southern California that employs the use of an external camera, mounted on a pair of glasses, connected to a microelectrode array by a connecting cable. The electrode array provides electrical stimulation directly to the ganglion cells. In clinical trials, a subject was able to perceive light on all 16 electrodes of the array, detect motion, and recognize simple shapes. This design has a distinct disadvantage in that it requires external hardware, such as glasses and the surgically implanted external device.

What is needed are improved and less surgically invasive retinal implants that can at least partially restore vision to patients suffering from vision loss resulting from the loss of photoreceptor cells as a consequence of retinal disease or damage.

SUMMARY

There is a great need for improved retinal implants that can improve the vision of those suffering from impaired vision that results from the loss of photoreceptor cells as a consequence of retinal disease or damage. Such retinal implants are provided herein. The described implants replace damaged photoreceptor cells, and therefore, can be used to treat any retinal disease or condition that has not destroyed the bipolar or ganglion network.

In one aspect, bacteriorhodopsin films are provided that include a plurality of individual layers of a bacteriorhodopsin protein, wherein each individual layer of the bacteriorhodopsin protein alternates with a layer of a cationic polymer, and wherein the bacteriorhodopsin protein is selected from the group consisting of a native (wild type) bacteriorhodopsin protein, a chloride pump mutant, a dipole mutant, a photocycle mutant, a gold-binding mutant, an ion pump mutant, and a combination thereof.

Additional bacteriorhodopsin films are disclosed that include a first main layer of a first bacteriorhodopsin mutant and a second main layer of a native bacteriorhodopsin protein, a second bacteriorhodopsin mutant, or a combination thereof. In certain embodiments, the first bacteriorhodopsin mutant is a gold binding mutant, and the first main layer includes about two to about five individual layers of the gold-binding mutant, wherein each individual layer of the gold-binding mutant is adjacent to a layer of a cationic polymer such that the first main layer contains alternating individual layers of the gold-binding mutant and the cationic polymer. In some embodiments, the second main layer comprises a native bacteriorhodopsin protein or a second bacteriorhodopsin mutant selected from the group consisting of a chloride pump mutant, a dipole mutant, a photocycle mutant, an ion pump mutant, and a combination thereof, and the second main layer comprises about 200 to about 400 individual layers of the native bacteriorhodopsin protein, second bacteriorhodopsin mutant, or combination thereof, wherein each individual layer of the native bacteriorhodopsin protein, second bacteriorhodopsin mutant, or combination thereof is adjacent to a layer of the cationic polymer such that the second main layer contains alternating individual layers of the native bacteriorhodopsin protein, second bacteriorhodopsin mutant, or combination thereof, and the cationic polymer.

In a second aspect, methods for producing a bacteriorhodopsin film are provided. The methods include the steps of: a) modifying a substrate to produce a negative surface charge on the substrate; b) depositing a layer of a cationic polymer upon the modified substrate; c) depositing an individual layer of a bacteriorhodopsin protein upon the layer of the cationic polymer, wherein the bacteriorhodopsin protein is a native bacteriorhodopsin or a bacteriorhodopsin mutant selected from the group consisting of a chloride pump mutant, a dipole mutant, a photocycle mutant, an ion pump mutant, and a combination thereof; d) depositing a layer of the cationic polymer upon the individual layer of the bacteriorhodopsin protein; e) depositing additional alternating layers of the bacteriorhodopsin protein and the cationic polymer as in steps (c) and (d) until about 200 to about 400 individual layers of the bacteriorhodopsin protein are deposited; thereby producing the bacteriorhodopsin film.

In another embodiment, the methods for producing a bacteriorhodopsin film include the steps of: a) depositing a layer of gold upon a substrate layer; b) depositing an individual layer of a first bacteriorhodopsin mutant upon the gold, wherein the first bacteriorhodopsin mutant is a gold-binding mutant; c) depositing a layer of a cationic polymer upon the individual layer of the gold-binding mutant of bacteriorhodopsin; d) depositing additional alternating layers of the gold-binding mutant of bacteriorhodopsin and the cationic polymer as in steps (b) and (c) until about two to about five individual layers of the gold-binding mutant of bacteriorhodopsin are deposited to form a main layer of the gold-binding mutant of bacteriorhodopsin; e) depositing a layer of the cationic polymer upon the last deposited layer of the gold-binding mutant of bacteriorhodopsin; f) depositing an individual layer of a native bacteriorhodopsin protein, second bacteriorhodopsin mutant, or combination thereof upon the layer of the cationic polymer, wherein the second bacteriorhodopsin mutant is selected from the group consisting of a chloride pump mutant, a dipole mutant, a photocycle mutant, ion pump mutant, and a combination thereof; g) depositing additional alternating layers of the native bacteriorhodopsin protein, second bacteriorhodopsin mutant, or combination thereof, and the cationic polymer as in steps (e) and (f) until about 200 to about 400 individual layers of the native bacteriorhodopsin protein, second bacteriorhodopsin mutant, or combination thereof have been deposited to form a main layer of the native bacteriorhodopsin protein, second bacteriorhodopsin mutant, or combination thereof; thereby producing the bacteriorhodopsin film. In certain embodiments, the substrate in the disclosed methods may be selected from the group consisting of polyethylene terephthalate, 2-hydroxyethyl methacrylate (HEMA), 2-phenylethyl methacrylate (PEM), polyethylene glycol (PEG), methyl methacrylate (MMA), polydimethylsiloxane (PDMS) macromer, polyvinyl alcohol (PVA) hydrogel. In other embodiments, the substrate is a platinum or titanium pin. In certain embodiments, the cationic polymer is poly(diallyldimethyl ammonium chloride).

In a third aspect, bacteriorhodopsin films produced by any one of the disclosed methods are provided.

In a fourth aspect, subretinal and epiretinal implants are provided that include any one of the bacteriorhodopsin films disclosed herein. In certain embodiments, the subretinal or epiretinal implant is flexible. The subretinal or epiretinal implants may further include a second substrate layer deposited upon the outermost layer of the bacteriorhodopsin film, wherein the second substrate layer is ion permeable. In some embodiments, the second substrate layer comprises a substrate selected from the group consisting of polyethylene terephthalate, 2-hydroxyethyl methacrylate (HEMA), 2-phenylethyl methacrylate (PEM), polyethylene glycol (PEG), methyl methacrylate (MMA), polydimethylsiloxane (PDMS) macromer, polyvinyl alcohol (PVA) hydrogel. In certain other embodiments, the subretinal or epiretinal implant is rigid. A rigid retinal implant is described herein that includes a plurality of pixels, wherein each pixel includes a bacteriorhodopsin film operatively associated with a platinum pin, and wherein the plurality of platinum pins is configured so as to interface with a ganglion cell layer or a bipolar cell layer of a patient's retina when implanted into the patient's eye. In one embodiment of the rigid retinal implant, the bacteriorhodopsin film is deposited upon a layer of gold deposited upon the tops of the platinum or titanium pins. In another embodiment of the rigid retinal implant, the bacteriorhodopsin film is deposited upon a layer of gold deposited on a pad, wherein each pixel comprises a gold covered pad contacting one of the platinum or titanium pins. The rigid subretinal or epiretinal implants may further include a second substrate layer deposited upon the outermost layer of the bacteriorhodopsin film, wherein the second substrate layer is a bionert material.

In a fifth aspect, flexible retinal implants are provided that include an inner substrate layer, a binder layer, an oriented film of bacteriorhodopsin protein layers, and an outer substrate layer.

In a sixth aspect, bacteriorhodopsin mutants are provided that contain one or more of the amino acid substitutions described herein and that are chloride pump mutants, dipole mutants, photocycle mutants, ion pump mutants, gold-binding mutants, or a combination thereof.

In a seventh aspect, methods are provided for treating a patient having loss of vision caused by loss of retinal photoreceptor cells, by implanting into an eye of the patient any one of the retinal implants disclosed herein, thereby treating the patient having loss of vision caused by loss of retinal photoreceptor cells. In certain embodiments, the retinal implant stimulates the bipolar cells of the eye of the patient by converting light into a proton or chloride ion gradient in the eye.

DETAILED DESCRIPTION

Described herein are protein films, flexible and rigid artificial retinal implants, and methods for making and using the implants to treat retinal diseases and conditions that cause vision loss resulting from degradation of retinal photoreceptor cells. The flexible implants contain a protein film that absorbs ambient light and produces an ion gradient for activating the retinal neural machinery. The rigid implants contain the same protein film, but in the rigid implants, the protein film absorbs ambient light and produces a photovoltaic signal for stimulating the neural machinery. The protein film contains the photosynthetic pigment bacteriorhodopsin, a light-driven proton pump transmembrane protein found in the purple membranes of halophilic archaea, or specialized genetically engineered mutants thereof. When the artificial retina is implanted into the eye, the bacteriorhodopsin film converts light entering the eye into a photovoltaic signal that simulates hyperpolarization of the photoreceptors. The bipolar cells provide an interface between the retinal photoreceptor cells and the optic nerve, which carries the stimulus to the visual centers of the brain, which process the visual stimuli.

Figure 1:
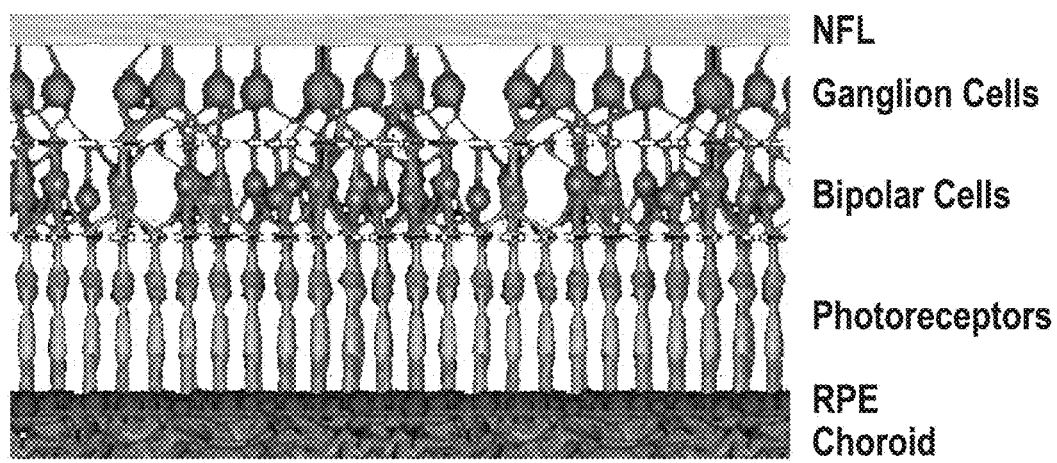
FIG. 1A is a schematic diagram showing the cell layers within a natural retina.
FIG. 1B is a schematic diagram of one embodiment of a flexible protein-based artificial retinal implant ("flexible retinal implant"), showing where the artificial retina is implanted with respect to a patient's natural cell layers when the implant is used for subretinal implantation. The flexible implant also may be used for epiretinal implantation. In certain embodiments, the implant uses a native bacteriorhodopsin or a genetically modified bacteriorhodopsin to pump a proton towards the bipolar cells and generate a nerve impulse via a local change in hydrogen ion concentration. In other embodiments, the implant uses a genetically modified bacteriorhodopsin that pumps chloride ions into the bipolar region. NFL refers to the nerve fiber layer, and RPE refers to the retinal pigment epithelium.
Figure 1:
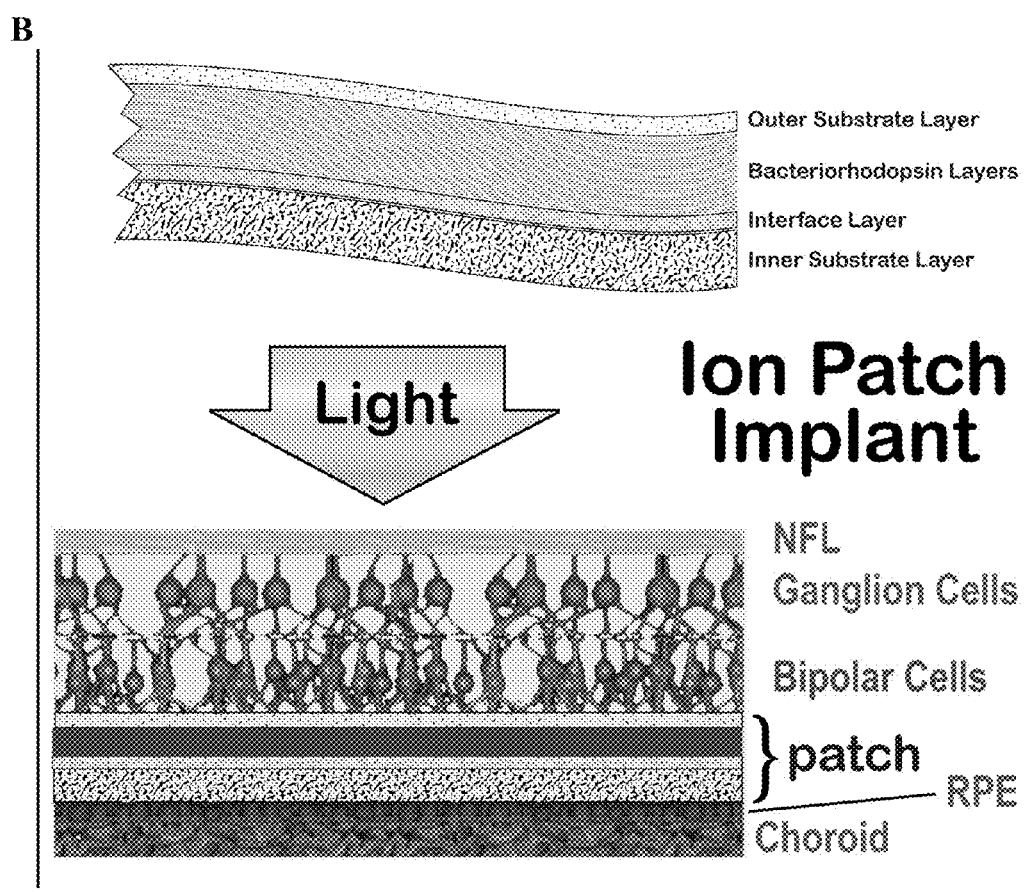

As an aid to understanding the structure and function of the natural retina, a simplified schematic diagram of the layers of the natural retina is shown in FIG. 1A. Photons of light enter the eye and pass through the nerve fiber layer (NFL; top of the diagram), ganglion cells, and bipolar cells respectively, prior to being absorbed by the photoreceptor cells (i.e., the rod cells and cone cells). Any light that is not intercepted by the photoreceptors is absorbed into the retinal pigment epithelium (RPE), which is attached to the choroid (vascular) layer at the back of the eye.

Described herein are two major groups of artificial retinas for subretinal or epiretinal implantation. The first major group includes flexible implants that stimulate bipolar cells by inducing an ion gradient in the local medium. One embodiment of the flexible implant utilizes layers of a native or genetically engineered mutant of the bacteriorhodopsin protein for creating a proton gradient to activate bipolar cells. A second embodiment of the flexible implant uses a different genetically engineered mutant of the bacteriorhodopsin protein which pumps a chloride ion in response to light absorption. The flexible implants described herein are designed to stimulate the bipolar cells that provide an interface between photoreceptors of the natural retina and the optic nerve as shown in FIG. 1A. The two embodiments of flexible artificial retina, and the components thereof, will be further described below.

The disclosed flexible artificial retinal implants generally comprise an inner substrate layer, a binder layer, an oriented film of protein layers, and an outer substrate layer (FIG. 1B). In certain aspects, the inner substrate layer comprises a synthetic polyethylene terephthalate (DACRON) microfiber. The binder layer in some aspects of the invention may comprise either gold or a cationic polymer such as poly(diallyl-dimethylammonium chloride) ("PDAC"). The oriented film of protein layers may comprise multiple layers of native bacteriorhodopsin and/or one or more mutant bacteriorhodopsin proteins, alternating with layers of a cationic polymer. In certain aspects, the outer substrate layer comprises an ion permeable layer of open weave DACRON microfiber or other ion permeable membrane.

The second major group of implants includes rigid artificial retinas for implantation over or under the retina (epiretinal and subretinal implants, respectively). The rigid artificial retinal implants described herein generally comprise a base carrying platinum pins. In the epiretinal implant, the top portion of each pin (i.e., the tip of the pin that faces the ambient light) is coated with gold. In the rigid subretinal implant, bottom portion of the platinum pin is associated with a gold covered pad. In both rigid implants, the gold carries a protein film containing multiple layers of bacteriorhodopsin. The first set of layers contains a bacteriorhodopsin mutant that has been genetically engineered to bind to gold. These gold-binding mutants of bacteriorhodopsin covalently attach in an oriented manner to the gold surface on the pixel pin. The second set of layers is based on a native bacteriorhodopsin or a bacteriorhodopsin mutant (high-Q bacteriorhodopsin) that has been optimized for both high dipole moment and efficient Q-state formation. The Q-state represents the off-state of the protein. If all of the protein on a pixel is converted into Q state, then the pixel no longer responds to light (the pixel is off). If 50% of the protein is converted into the Q state, then the pixel gives off a signal that is one-half as large as a standard pixel (the pixel is turned down). Calibration of the rigid artificial retina after implantation into a patient's eye by adjusting the response of the individual pixels to light is described below. The rigid subretinal or epiretinal implants may further include a second substrate layer deposited upon the outermost layer of the bacteriorhodopsin film, wherein the second substrate layer is a bionert material.

DEFINITIONS

As used in this specification, the singular forms "a," "an," and "the" include plural referents unless expressly and unequivocally limited to one referent.

As used herein, the term "film" refers to a plurality of individual protein layers. In some embodiments, the film includes alternating layers of a cationic polymer and individual protein layers.

The terms "wild-type bacteriorhodopsin" and "native bacteriorhodopsin," as used herein, both refer to a form of bacteriorhodopsin as it occurs in nature. One example of wild type or native bacteriorhodopsin is bacteriorhodopsin from the host organism *Halobacterium salinarum*. This organism also has been known by several pseudonyms, of which the most common are *Halobacterium halobium* and *Halobacterium salanarium*.

Further, as used herein, the terms "mutant bacteriorhodopsin," "bacteriorhodopsin mutant," "genetically engineered bacteriorhodopsin," "mutated bacteriorhodopsin," and the like all refer to a bacteriorhodopsin protein in which at least one amino acid of the wild-type bacteriorhodopsin protein has been replaced with a different amino acid not found at that amino acid position within the wild-type bacteriorhodopsin.

As used herein, the terms "gold-binding bacteriorhodopsin," "gold-binding mutant," and the like refer to a bacteriorhodopsin molecule that has been genetically engineered (i.e., one or more of the wild-type amino acid residues has been replaced with a cysteine residue) to bind to gold more strongly than does the wild-type bacteriorhodopsin molecule.

As used herein, the terms "enhanced dipole mutant bacteriorhodopsin," "dipole mutant bacteriorhodopsin," "dipole mutant," and the like refer to a bacteriorhodopsin molecule that has been genetically engineered (i.e., one or more of the wild-type amino acid residues has been replaced with a different residue) to have a change in the overall charge of the protein, increasing the intrinsic dipole movement of the protein such that the mutant protein provides a larger photochemical response in thin films than does wild-type bacteriorhodopsin.

As used herein, the terms "fast photocycle mutant bacteriorhodopsin," "photocycle mutant bacteriorhodopsin," "fast photocycle mutant," "photocycle mutant," and the like refer to a bacteriorhodopsin molecule that has been genetically engineered (i.e., one or more of the wild-type amino acid residues has been replaced with a different residue) such that the mutant protein pumps ions more rapidly than does wild-type bacteriorhodopsin.

As used herein, the terms "chloride pump mutant bacteriorhodopsin," "chloride mutant," and the like refer to a bacteriorhodopsin molecule that has been genetically engineered (i.e., one or more of the wild-type amino acid residues has been replaced with a different residue) such that the mutant protein pumps chloride ions instead of protons in response to light absorption.

As used herein, the terms "ion pump mutant bacteriorhodopsin," "ion pump mutant," and the like refer to a bacteriorhodopsin molecule that has been genetically engineered (i.e., one or more of the wild-type amino acid residues has been replaced with a different residue) such that the mutant protein pumps ions more rapidly than does wild-type bacteriorhodopsin.

As used herein, the term "main layer" refers to a stratum within a bacteriorhodopsin film that contains two or more layers of a single type of bacteriorhodopsin protein. For example, in certain embodiments, the bacteriorhodopsin films of the invention may contain a main layer of a bacteriorhodopsin gold-binding mutant (containing two to five individual layers of the gold-binding mutant) and a main layer of a native bacteriorhodopsin, bacteriorhodopsin dipole mutant, photocycle mutant, chloride pump mutant, ion pump mutant, or combination thereof (containing about 200-400 individual layers of the native or mutant protein). In other embodiments, the bacteriorhodopsin film may comprise only a native bacteriorhodopsin, bacteriorhodopsin dipole mutant, photocycle mutant, chloride pump mutant, ion pump mutant, or combination thereof (containing about 200-400 individual layers of the native protein or mutant).

As used herein with respect to the flexible retinal implants, the terms "inner substrate layer" and "outer substrate layer" refer to a layer of a biocompatible material for use in the disclosed retinal implants. In some embodiments, the substrate layer is a flexible fabric or weave of the substrate. As used herein with respect to the rigid retinal implants, the term "substrate" refers to a platinum or titanium pin or other suitable rigid structure for layering of the bacteriorhodopsin film.

As used herein, the term "binder" refers to a molecule or substance that allows a bacteriorhodopsin protein or mutant to bind to a substrate layer of the retinal implant.

As used herein, the term "retinal implant" is used to refer to implants for both epiretinal and subretinal implantation, unless otherwise specified.

As used herein, the term "retinal patch," "retinal ion patch," "ion patch," "flexible retinal implant," and the like are used interchangeably to refer to the flexible artificial protein-based retinal implants disclosed herein.

As used herein, the term "pixel" of an artificial retina implant refers to a platinum or titanium pin or other suitable rigid structure carrying a film of gold, upon which has been deposited a bacteriorhodopsin film, which contains a main layer of gold-binding bacteriorhodopsin and a main layer of native or Q-mutant bacteriorhodopsin. Alternatively, a "pixel" can be a platinum or titanium pin or other suitable rigid structure physically associated with a gold covered pad onto which has been deposited a main layer of gold-binding bacteriorhodopsin and a main layer of native or Q-mutant bacteriorhodopsin.

As used herein, the term "surgical handle" refers to a hole, loop, ring, bracket, or other device by which the artificial retinal implants described herein can be surgically fastened, i.e., implanted, within the eye.

Ion Gradient-Inducing Flexible Protein-Based Artificial Retina

A flexible protein-based artificial retinal implant is described herein based on the use of a protein, bacteriorhodopsin, to convert light into an ionic gradient that activates the retinal bipolar cells by inducing an ion gradient in the local medium. Bacteriorhodopsin (BR) is a light-driven proton pump isolated from the salt-marsh archaeon, *Halobacterium salinarum*. The light-transducing protein isolated from the purple membrane of this organism has a quantum efficiency identical to rhodopsin, the native protein in the rod outer segments of the eye. However, bacteriorhodopsin has three orders of magnitude greater thermal and photochemical stability than rhodopsin. The native bacteriorhodopsin protein pumps a proton in response to light absorption, and in one embodiment of the retinal patch, a proton gradient is used to activate the bipolar cells. Mutant forms of this protein may be created as discussed further below that have increased intrinsic dipole moment, that pump ions more rapidly, that have gold-binding properties, or that have a combination of these traits. In addition, the protein can also be converted into a chloride ion pump through genetic engineering of the protein. The use of one or more of these wild-type and/or genetically engineered bacteriorhodopsin proteins in a flexible retinal implant will result in a visual signal in a patient.

The disclosed flexible retinal implants will not require external camera equipment or the need for an external power supply. Furthermore, no cable will be required to connect external hardware to stimulate electrodes within the eye, because the disclosed retinal implants do not contain electrodes. The introduction of the disclosed flexible retinal implants is surgically less invasive and lessens the chance of infection as compared to currently available retinal implants. Another unique capability of the proposed implant design is the ability of bacteriorhodopsin to form an inactive state, called the Q state as discussed further below, which allows for pixel mediation where extraneous pixels in the implant can either be turned down or off. This feature is of significant advantage because it provides a non-invasive method for optimizing the coupling of the implant to the nerve cells. For example, a patient would describe "hot spots" in the perception field, and these would be characterized by pixels that selectively overactivate a bipolar cell. This position is identified using a microscope arrangement which looks into the back of the eye and is able to focus on the implant with near-diffraction limited performance. The optical design allows the microscope to individually activate pixels using a weak laser, and to selectively pulse a pixel using a sequence of two red laser pulses with temporal profiles appropriate for converting the bacteriorhodopsin in that region to the Q state. Full conversion is possible, but selective conversion will dim the pixel. In this fashion, the overresponse of individual pixels can be mediated, and if necessary, turned off entirely.

The disclosed flexible retinal implants have many additional distinct advantages over the current leading technologies. They are flexible and thin, and can be inserted in the subretinal space and accommodate any shape or size of eye. Individual pixels can be turned off or turned down by using low-power red laser light as discussed above. Two different ion mechanisms of activation, as discussed further below, are available to enhance flexibility and handle a larger range of patient conditions. The materials used on the inner and outer surfaces of the retinal implants (e.g., a DACRON inner layer and a DACRON ion permeable outer layer) provide long-term stability within the body without activating an immune response in the patient. In certain embodiments, the subretinal implant uses DACRON as the base fabric, which is bioinert, flexible, and can be chemically modified to stabilize layers of bacteriorhodopsin mutants. Microfiber based fabrics also provide for ion transport while protecting the bacteriorhodopsin proteins.

Figure 2:
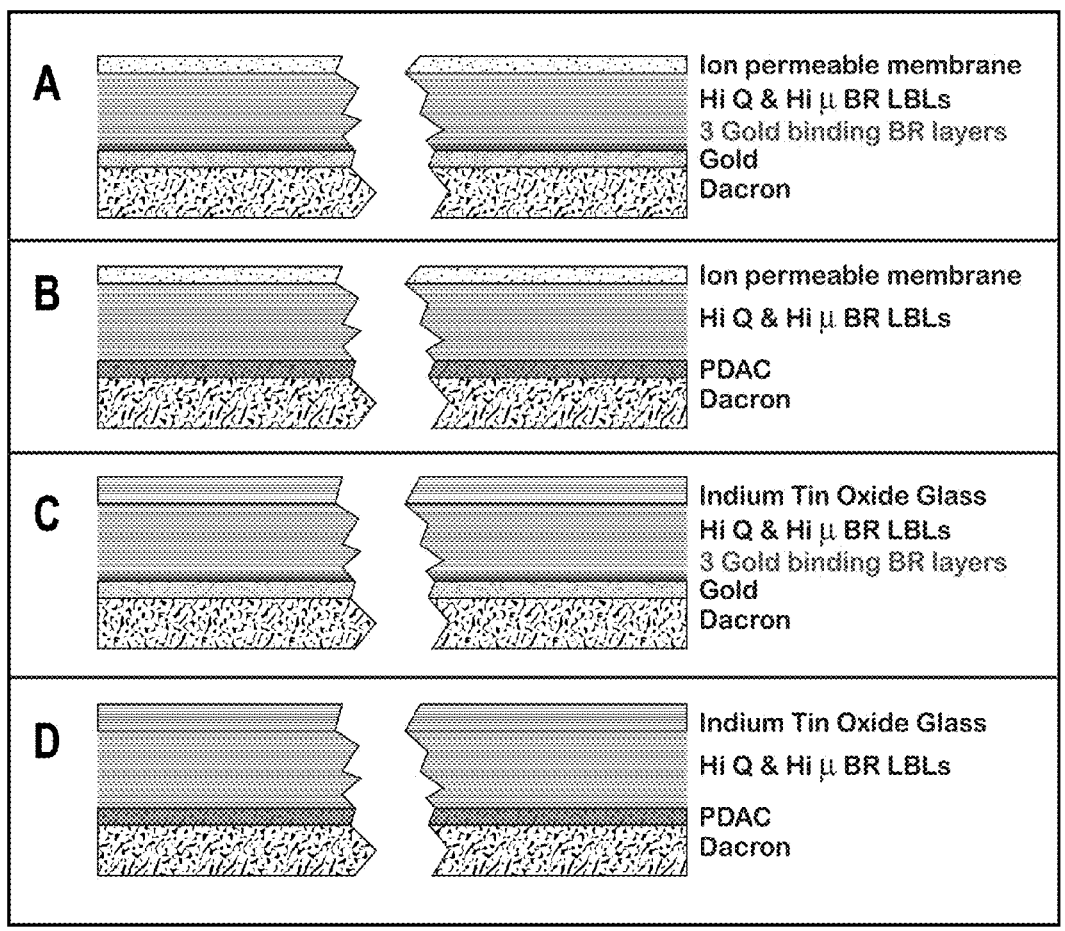
FIG. 2 is a schematic diagram of two different embodiments of the disclosed flexible protein-based artificial retinas showing the general structure of an inner substrate layer, a binder layer, an oriented protein film of bacteriorhodopsin layers, and an outer substrate layer. Both embodiments are shown with DACRON as the inner substrate layer, and an ion permeable membrane as the outer substrate layer. Hi Q mutants are those which have a higher efficiency for photochemically entering the inactive Q state. Hi dipole mutants are those which have a larger dipole moment in the resting state, and form tighter packing films which enhances the photochemically generated ion gradient. LBLs refers to the layer by layer film of bacteriorhodopsin proteins. Panel A shows an embodiment that includes gold as the binder for the bacteriorhodopsin layers, and Panel B shows poly(diallyldimethyl ammonium chloride) (PDAC) as the binder for the bacteriorhodopsin protein. Panels C and D are schematic diagrams of analogous artificial retinas for testing purposes. These structures have the outer substrate layer replaced with a glass slide coated with indium tin oxide, such that ion transport may be measured using an electrometer.

The disclosed flexible subretinal implants are intended to be implanted between the photoreceptor layer and the retinal pigment epithelium (RPE) layer of the patient's retina (FIG. 1B). FIG. 1B shows a schematic of one embodiment of the flexible protein-based subretinal implants of the invention implanted in the natural cell layers of the patient's eye. FIG. 2 is a schematic diagram of two different embodiments of the disclosed flexible protein-based artificial retinas showing the general structure of an inner substrate layer, a binder layer, an oriented protein film of bacteriorhodopsin layers, and an outer substrate layer. Both embodiments are shown with DACRON as the inner substrate layer, and an ion permeable membrane as the outer substrate layer. Panel A shows an embodiment that includes 10 Å of gold sputtered onto the DACRON inner substrate layer which has been heated to above the glass transition temperature. This gold layer serves as the binder for gold-binding bacteriorhodopsin mutants. Panel B shows poly(diallyldimethyl ammonium chloride) (PDAC) as the binder for the initial layer of bacteriorhodopsin protein. The initial layers in both embodiments are followed by additional layers of bacteriorhodopsin proteins (e.g., native, dipole mutant, photocycle mutant, chloride pump mutant, ion pump mutant, or combinations thereof). Panels C and D of FIG. 2 are schematic diagrams of analogous artificial retinas for testing purposes. These structures have the outer substrate layer replaced with a glass slide coated with indium tin oxide, such that ion transport may be measured using an electrometer. The disclosed flexible retinal implants are also designed for epiretinal implantation.

The mechanism of operation of the disclosed flexible retinal implants is simple, although the physiology of action is very complex. It is known that altering the pH or ion concentration near a bipolar or ganglion cell can trigger a nerve impulse. Simulations suggest that the mechanism of this process is often due to indirect manipulation of or competition with the native signal carriers. The disclosed retinal implants take advantage of this phenomenon, using a native or mutant protein-based design, in order to restore vision in a patient. In the native organism *Halobacterium salinarum*, bacteriorhodopsin (BR) serves as a light-driven proton pump that operates with a quantum efficiency of 0.65, identical to that of the visual pigment rhodopsin. *H. salinarum* also has a chloride ion pump in the outer membrane, called halorhodopsin, which pumps a chloride ion in response to light excitation. Both proton pump and chloride ion pump based retinal implants are desirable and are disclosed herein. However, because halorhodopsin is comparatively fragile, a bacteriorhodopsin mutant, which converts bacteriorhodopsin from a proton pump to a chloride ion pump, is used in some embodiments of the retinal implants in order to achieve long-term stability of the implant. The available literature indicates that a proton gradient will be more efficient, but that a chloride ion gradient will cause less long-term damage to neural tissue.

The flexible retinal implants disclosed herein represent a significant improvement over the electrical stimulation counterparts that currently dominate current methods of treatment. The Ph.D. thesis of Dr. Luke S. K. Theogarajan investigated the potential of ion-based retinal implants using sophisticated computational modeling (2007, Dept. of Electrical Engineering and Computer Science, MIT). He demonstrated, via simulation, that proton ($H^+$), potassium ($K^+$) or chloride ($Cl^-$) ion gradients would activate the retinal neural machinery and proposed an implant based on bacteriorhodopsin. His model implant, however, would not have worked because he used only one layer of bacteriorhodopsin which would not yield adequate light capture capability. Theogarajan was not the first to propose ion gating. It has long been known that altering the pH or ion concentration near a bipolar or ganglion cells can trigger a nerve impulse (See, e.g., Enz et al., 1999, J. Neurosci. 19:9841-47; Bringmann et al., 1997, Glia 19:311-23; Verweij et al., 1996, Vision Res. 36:3943-53; Marc, 1999, J. Compar. Neurol. 407:65-76; Konnerth et al., 1987, J. Physiol. 386:603-33; and Ettaiche et al., 2004, J. Neurosci. 24:1005-12). Studies of channelrhodopsins provide additional support for the viability of ion gradient implants (See, e.g., Bamann et al., 2008, J. Mol. Biol. 375:686-94; Berthold et al., 2008, Plant Cell 20:1665-77; Douglass et al., 2008, Current Biol. 18:1133-37; Nagel et al., 2002, Science 296: 2395-98; Nagel et al., 2003, PNAS 100:13940-45; and Petreanu et al., 2007, Nature Neurosci. 10:663-68).

The bipolar cell system of the eye is very complex and involves two types of bipolar cells characterized as on-center or off-center (on- or off-bipolar cells). Both types monitor the photoreceptor cells and selectively activate or suppress ganglion activity based on whether a photoreceptor cell is depolarized (in the dark) or hyperpolarized (illuminated). Electrical stimulation of the bipolar cells is complicated by the fact that activating an off-bipolar cell via an electrical impulse can negate the nearby activation of an on-bipolar cell. The present retinal implants have a distinct advantage over electrical stimulation-based implants because ion currents automatically discriminate by simulating hyperpolarization of the photoreceptor. This feature avoids the above problem of activating the wrong cells, and also leads to a lower current requirement (i.e, fewer ions can simulate electronic effects).

Epiretinal Rigid Protein-Based Artificial Retina

The rigid epiretinal implant described herein is implanted on top of the natural retina. The rigid epiretinal implant contains platinum pins to activate ganglion nerve cells of the natural retina because platinum is highly conductive and yet completely inert to the body. When implanted, the platinum pins of the rigid epiretinal implant extend down through the nerve fiber layer of the patient's natural retina into the ganglion cells. The length of these pins can vary from about 0.2 mm to about 1.5 mm and is determined by the nature of the patient's retinal disease and the decision to provide ganglion versus bipolar stimulation via the retinal implant. The top end of each platinum pin is coated (from the bottom moving upward) with: a layer of gold, a main layer of gold-binding bacteriorhodopsin molecules, and a main layer of native or mutant bacteriorhodopsin molecules. The tops of the pins are immobilized into a base plate. Specifically, each pin is inserted into its own hole that is slightly larger than the diameter of the pin and that passes entirely through the thickness of the base plate. The base plate is covered by a transparent window of conducting plastic to allow light to pass through to the bacteriorhodopsin layers. A single platinum pin carrying its bacteriorhodopsin film within a rigid artificial retinal implant is referred to herein as a "pixel." The rigid artificial retinal implants described herein can be made with various numbers of pixels. Using a larger number of pixels will allows an artificial retinal implant to provide a greater level of visual resolution to the patient. For example, artificial retinal implants can be made in arrays of about 400×300 pixels (approximately the resolution of a television), about 800×400 pixels (or greater), or anything in between.

Figure 3:
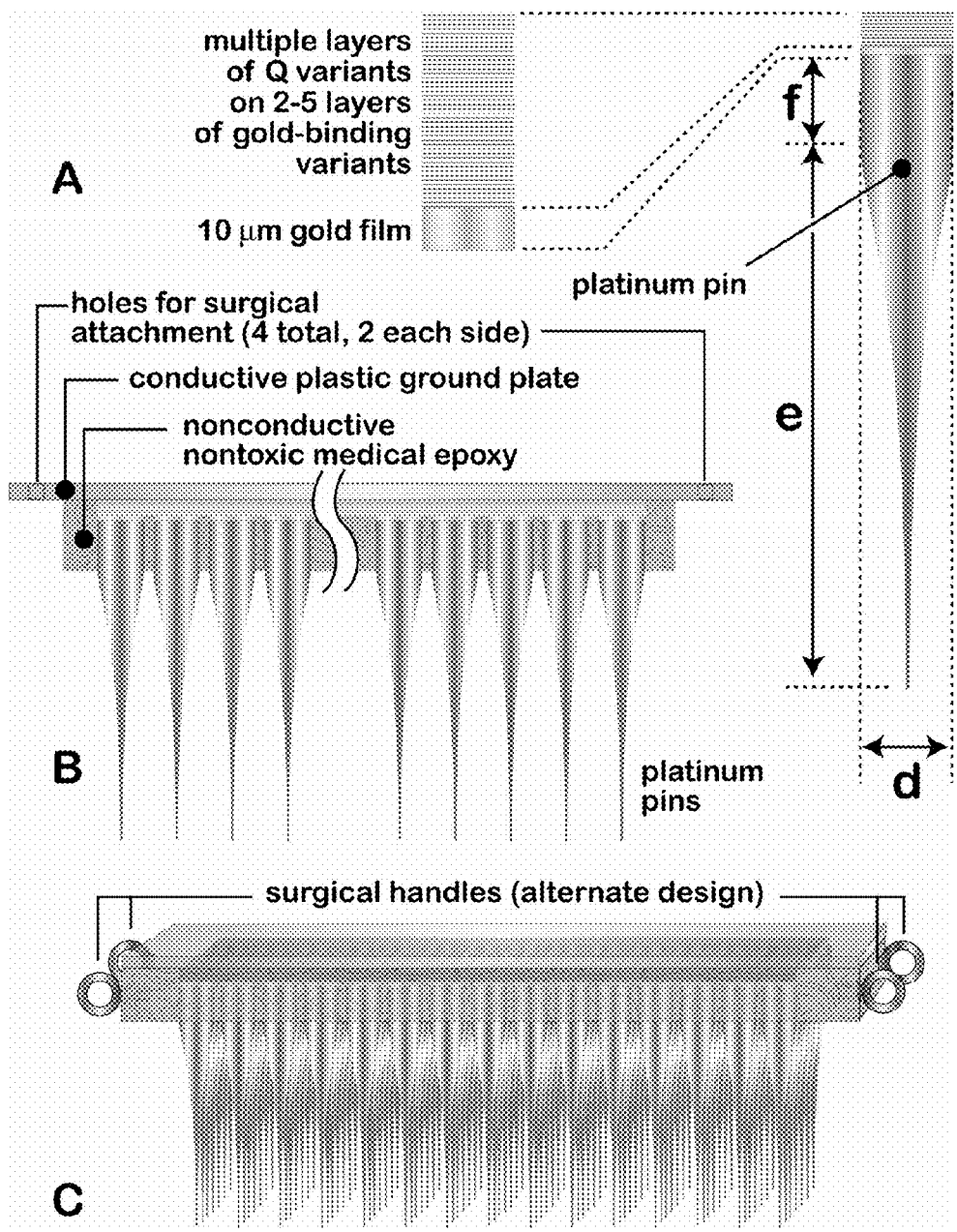
FIG. 3 shows schematic diagrams of two embodiments of a rigid artificial retina for epiretinal implantation (a "rigid epiretinal implant"). Panels A and B are schematic diagrams showing the configuration of the platinum pins and bacteriorhodopsin protein layers in one embodiment of the rigid epiretinal implant. This embodiment has a conductive plastic ground plate including four holes for surgical attachment of the implant to the patient's eye. Although the figure indicates that mutant bacteriorhodopsin proteins are used, native bacteriorhodopsin also may be used in this epiretinal implant. Panel C is a schematic diagram showing an alternative embodiment of the rigid epiretinal implant, which includes surgical handles. Panel D is a schematic diagram of one embodiment of the rigid epiretinal implant, showing where the artificial retina is implanted with respect to a patient's natural cell layers. The implant is shown with probe lengths optimized to intercept the ganglion cells directly underneath the nerve fiber layer of the natural retina.
Figure 3:
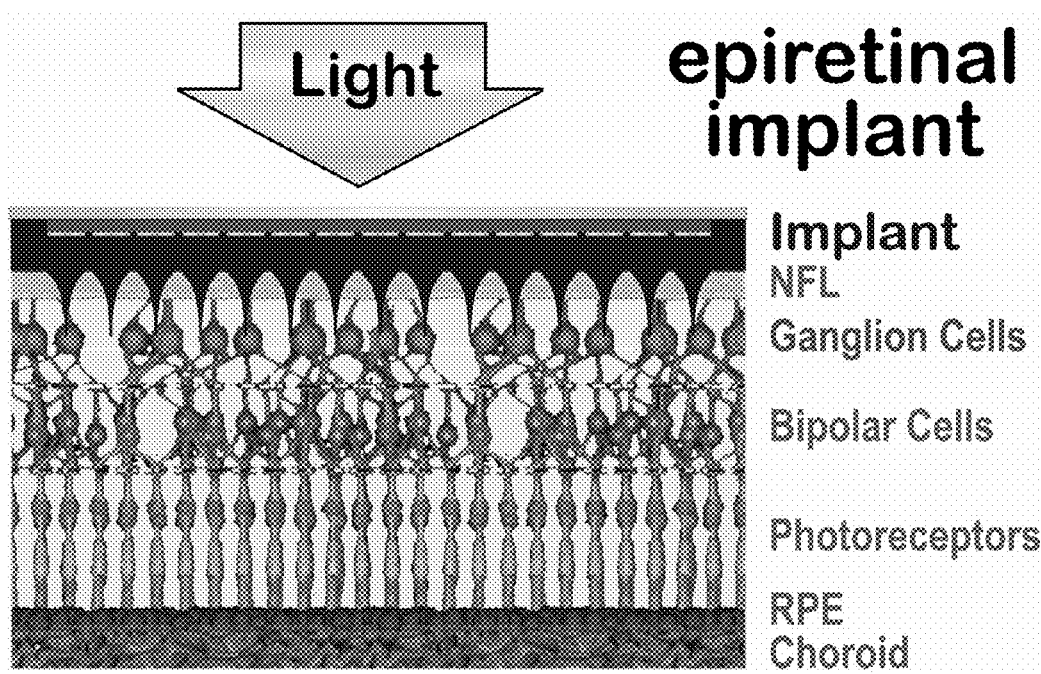

FIG. 3A is a schematic diagram of an individual pixel within an epiretinal implant of the invention showing, from the top of the platinum pin moving upwards, an approximately ten-micron layer of gold, a main layer of gold-binding bacteriorhodopsin containing about two to about five sublayers of gold-binding bacteriorhodopsin molecules and a main layer of native or mutant bacteriorhodopsin, containing about 200 to about 400 sublayers of native or mutant bacteriorhodopsin molecules. The mutant bacteriorhodopsin may be, for example, a dipole mutant, photocycle mutant, or combination thereof. Q mutant bacteriorhodopsin molecules that also have enhanced dipole moments can be used to produce the bacteriorhodopsin films and rigid artificial retinas described herein. Although not wishing to be bound by theory, bacteriorhodopsin mutants with enhanced dipole moments can enhance the efficiency of the bacteriorhodopsin films and rigid artificial retinas described herein by allowing more consistent orientation of the bacteriorhodopsin molecules and/or denser packing of the bacteriorhodopsin molecules within the films. Suitable mutants are described further below.

FIG. 3B is a diagram of a side view of a single row of pixels showing the nonconductive, nontoxic medical epoxy enclosure that is applied to the lateral and bottom surfaces of the base plate to seal and protect the bacteriorhodopsin layer on all five sides (with the exception of the side at the top of the implant, which is covered by the transparent window of conducting plastic). Suitable epoxies are nontoxic, nonconducting, transparent epoxies that can be used in medical implants. There are many epoxy formulations that can be used, including those made by Epoxy Technology Corp. (for example, Product Nos. 301, 320, and 354, Epoxy Technology, 14 Fortune Drive, Billerica, Mass. 01821). Suitable conductive plastic materials are bioinert materials and are well known in the art (See, e.g., U.S. Pat. No. 7,291,540, Xie et al., 2002, Bioscience Rep 21, 513-536; Xu et al., 2005, Tissue Eng 11, 1736-1748; Shi et al., 2005, Eng Mat 6, 485-490; Lloyd et al., 2001, Biomaterials 22, 769-785; Montezuma et al., 2006, Invest Ophth V is Sci 47, 3514-3522; Weiland et al., 2005, Annu. Rev. Biomed. Eng. 7, 361-401; and Scholz, 2007, J Bioact Compat Pol 22, 539-568 for suitable materials). In one implementation, the transparent plastic window extends beyond the epoxy seal and contains two holes at each of two opposite sides of the implant to provide four holes total (e.g., one at approximately each corner of the implant) to provide surgical handles. The surgical handles can be located in any position in which the handles do not interfere with transmission of light to the pixels.

FIG. 3C is a diagram of a perspective view of an epiretinal implant as described herein showing an alternative design using rings for the surgical handles. The surgical handle "rings" need not be circular rings as shown in the diagram, but rather they can be any shape (e.g., oval, pyramidal, triangular, rectangular, square, etc.) that will allow a surgeon to securely attach the rigid epiretinal implant to the patient's natural retina. The surgical handles can be made of any substrate that is appropriate for a surgical implant (e.g., titanium). The side of the rigid implant of FIG. 3C is shown as partially transparent so that the underlying structure can be shown. Light enters the epiretinal implant from the top and is absorbed by the bacteriorhodopsin layers beneath the transparent conducting plastic that seals the bacteriorhodopsin film from the vitreous humor within the patient's eye.

FIG. 3D is a schematic diagram of a rigid epiretinal implant implanted on top of the natural retina. The length of the platinum pins of the epiretinal implant are optimized to intercept the ganglion cells directly beneath the nerve fiber layer (NFL). Shown beneath the ganglion cell layer is the bipolar cell layer, the photoreceptor cell layer, the retinal pigment epithelium (RPE), and the choroid (vascular) layer. A key feature of the epiretinal implant shown in FIG. 3D is that the platinum pins directly activate the ganglion cells. An advantage of this design is that the implant is in the direct path of the light after the light passes through the vitreous humor of the eye.

Two basic forms of the rigid epiretinal implant are described herein. The first is a standard design in which the platinum pin lengths extend only so far as to intercept the ganglion cells within the natural retina. The alternative design employs longer pin lengths that reach beyond the ganglion cell layer to intercept and thereby stimulate the bipolar cells (i.e., the cell layer beneath the ganglion cell layer in the natural retina). The longer pins allow direct activation of the bipolar cells, which allows for higher sensitivity and the use of smaller pixels and thus higher resolution of the imaging process. This alternative implementation requires deeper penetration into the retinal tissues and the alternative surgical attachments (the ring-like attachments) shown in FIG. 3C provide a more secure attachment.

The Rigid Subretinal Protein-Based Artificial Retina

Figure 4:
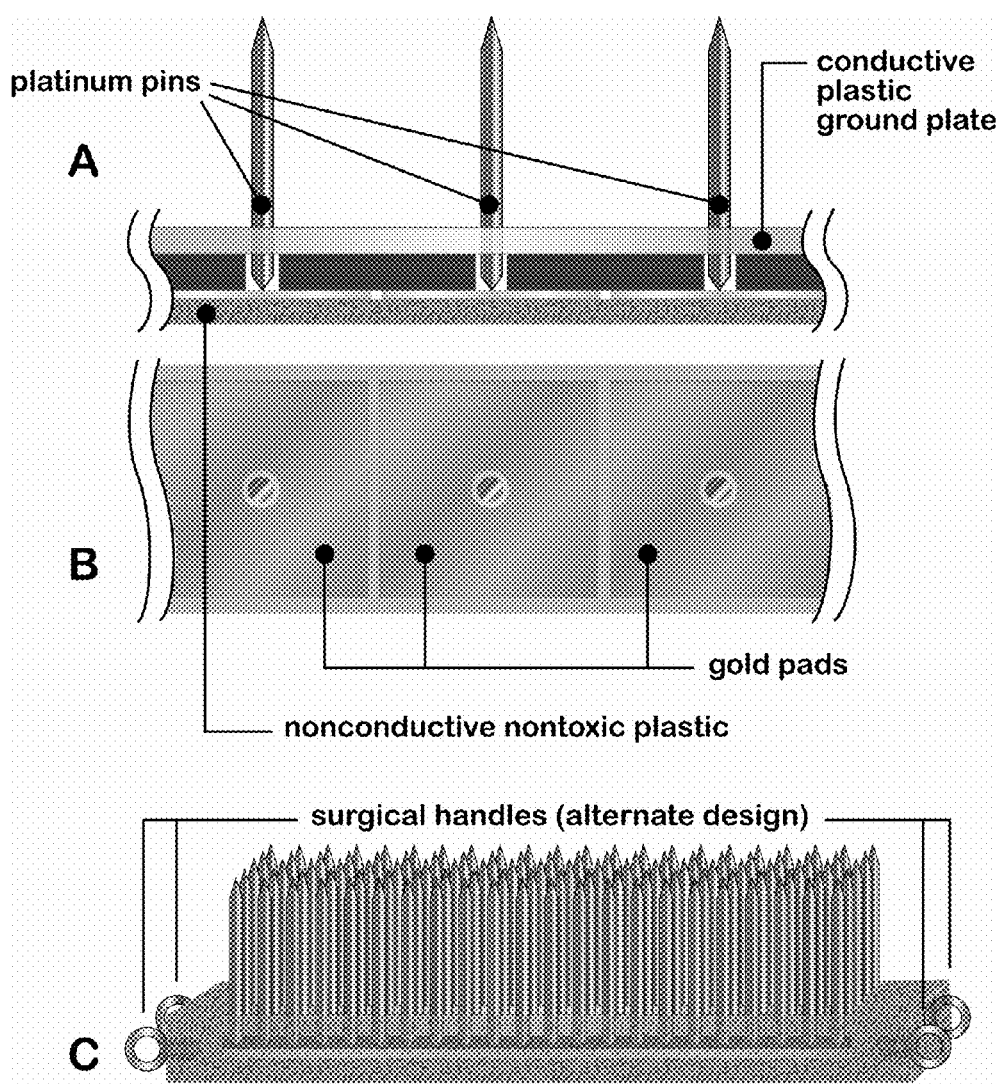
FIG. 4 shows schematic diagrams of two embodiments of a rigid artificial retina for subretinal implantation (a "rigid subretinal implant"). Panels A and B are schematic diagrams of a side view and top view, respectively, of one embodiment of the rigid subretinal implant. Panel C is a schematic diagram showing an alternative embodiment of the rigid subretinal implant, which includes surgical handles. Panel D is a schematic diagram of one embodiment of the rigid subretinal implant inserted between the retinal pigment epithelium and the photoreceptor cells of the natural retina.
Figure 4:
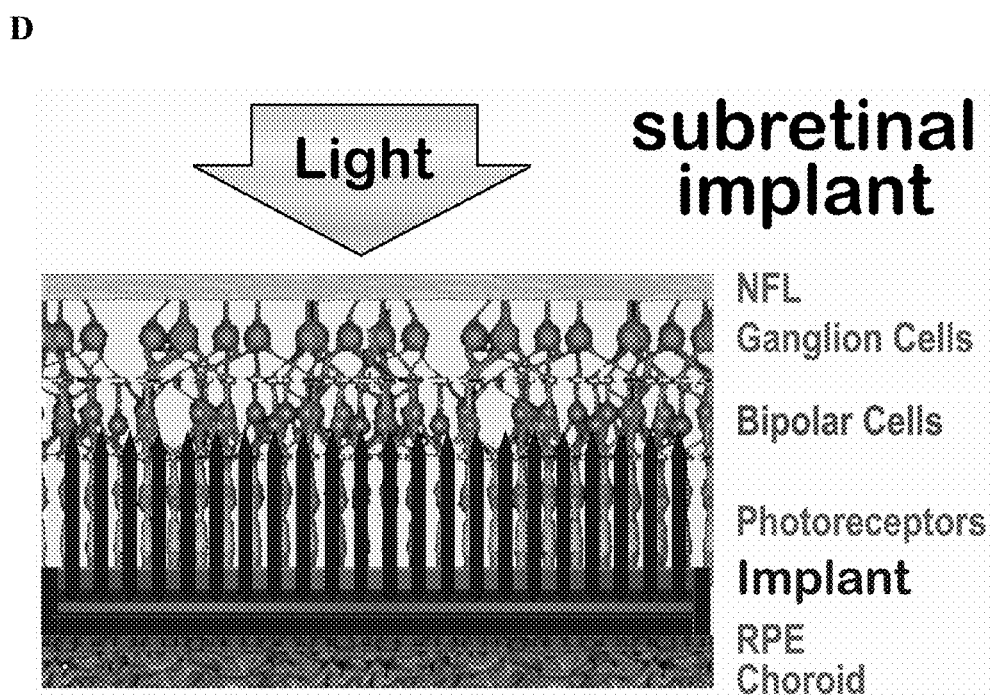

The rigid subretinal implant is implanted between the photoreceptor layer and the retinal pigment epithelium (RPE) layer of the patient's retina. FIG. 4 includes diagrams of the protein-based rigid subretinal implants of the invention. FIG. 4A is a close-up side view of a rigid subretinal implant showing, from the bottom moving upward, a base plate of nonconductive, nontoxic plastic; gold covered pads; bacteriorhodopsin film; platinum pins wherein one pin is associated with each gold covered pad, with one end of the pin disposed against the pad; a main layer of gold-binding bacteriorhodopsin deposited onto each gold covered pad, a main layer of native or mutant bacteriorhodopsin deposited onto the main layer of gold-binding bacteriorhodopsin, a transparent conductive plastic ground plate through which each platinum pin passes via a hole slightly larger than the diameter of the pin; between the layer of gold covered pads and the conductive transparent window. A layer of transparent, non-toxic, non-conducting epoxy surrounds each platinum pin (i.e., between the pin and the hole in the clear plate through which the pin passes so as to seal each pin).

Each pixel of the rigid subretinal implant comprises a pin, a gold covered pad, and a bacteriorhodopsin film (containing a main layer of gold-binding bacteriorhodopsin and a main layer of native or mutant bacteriorhodopsin) deposited upon the gold covered pad. Use of a separate gold covered pad for each pin avoids cross-talk between the pixels. Photons of light entering the eye passes through the clear conductive plastic plate and are absorbed by the bacteriorhodopsin protein film. The electrical current generated by photon-activated bacteriorhodopsin travels along the platinum pins and is transferred to bipolar cells of the patient's natural retina via the pins. The bacteriorhodopsin is oriented using a layer-by-layer method such as described herein, which provides for rigorous control of the number of layers of protein and hence the optical density of the protein-based pixel.

FIG. 4B is a schematic diagram showing a top view of the gold covered pads and platinum pins of the rigid subretinal implant shown in FIG. 4A. FIG. 4C is a schematic diagram showing a side view of the rigid subretinal implant showing the base plate of nonconductive, nontoxic plastic, the platinum pins, and the surgical handles of alternative design (ring handles) as described for the rigid epiretinal implant above.

FIG. 4D is a schematic diagram showing a side view of the rigid subretinal implant inserted between the retinal pigment epithelium and the photoreceptor cell layer of the natural retina. The platinum pins interface with and send signals to the bipolar cells. Shown from top to bottom in FIG. 4D is the nerve fiber layer, the ganglion cell layer, the bipolar cell layer with interfacing platinum pins, the photoreceptor cell layer with platinum pins passing through the layer, the base plate and associated structures of the subretinal implant, the retinal pigment epithelium, and the choroid (vascular) layer.

The implant is shown in FIG. 4D with probe lengths optimized to intercept the bipolar cells directly above the photoreceptor cells in the natural retina. In one embodiment of this design, the probes are coated with a nonconducting bioinert polymer while leaving one micron of the tip exposed (uncoated). The coating may be polyisoprene, which is a good insulator and bioinert. The process is a two step process. The tips are protected by embedding them in a solgel prior to polymerization, and then allowing the polymerization to take place. Then aerosol assisted chemical vapor deposition (AACVD) is used to introduce polyisoprene to the unprotected pins and the bottom of the implant. The tips of the pins are subsequently exposed by carefully pealing the solgel film away. This process enhances the signal coupling to the nerve cells by preventing signal loss to surrounding tissue. The process is only necessary when longer pins, designed to intercept the bipolar cells, are used. But the process always enhances signal coupling and is the recommended design.

The subretinal implants are more difficult to implant than the epiretinal implants, because implantation requires that the surgeon separate the photoreceptor cell layer from the retinal pigment epithelium layer and insert the implant in between the two layers (See, e.g., Zrenner, E. (2002) The Subretinal Implant: Can Microphotodiode Arrays Replace Degenerated Retinal Photoreceptors to Restore Vision? *Ophthalmologica* 21651, 8-20; Cohan, E. D. (2007) Prosthetic interfaces with the visual system: biological issues. *J. Neural Eng.* 4, R14-R31; and Zrenner, E. (2008) Will Retinal Implants Restore Vision? Science 295, 1022-1025). Implantation of the subretinal implants of the invention can damage the photoreceptor cells of the patient's natural retina. However, this damage is of little consequence, since a retinal implant would not be required if the photoreceptor cells were functioning properly. The rigid subretinal implant in effect replaces or mingles with the photoreceptors, and the platinum pins impregnate and stimulate the bipolar cells. The advantage of the rigid subretinal implant compared to the rigid epiretinal implant is that only a small current is required to stimulate the bipolar cells. However, photons of light must first pass through the nerve fiber layer, ganglion cells, bipolar cells, and any remaining photoreceptors before the photons can activate the protein film of the rigid subretinal implant.

Substrate Layers

In some embodiments, the inner substrate layer (or posterior surface) of the flexible retinal implant is assembled using a fabric or other weave of a modified synthetic DACRON microfiber (Goodfellow Cambridge Limited), a medically inert (bioinert) material. DACRON is the trade name of polyethylene terephthalate, which is the polymeric molecule shown below:

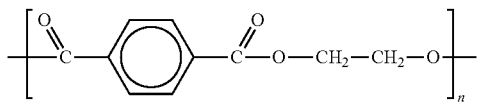

This polymer has been successfully used in both sutures and retinal implants. An advantage of DACRON is that it provides a convenient set of methods for attaching and orienting protein directly on the fiber surface. The wild type and/or mutant bacteriorhodopsin protein may be attached to the DACRON microfiber via direct binding to a thin gold sputtered layer or by electrostatic adsorption methods as described below.

In some embodiments, the outer substrate layer is a thin open weave DACRON fabric which acts as an ion permeable membrane, and which is attached to the outermost protein layer of the implant using the same procedures as used to attach the protein layers to the thicker DACRON base fabric of the inner substrate layer.

In some embodiments, the inner substrate layer is ES308704 Polyethylene terephthalate (Mesh Nominal Aperture: 21 μm, Monofilament diameter: 41 μm, Threads/cm: 163, Open area: 12%, Type: Plain weave mesh). In some embodiments, the outer substrate layer is an ion-permeable fabric ES308710 Polyethylene terephthalate (Mesh Nominal Aperture: 100 μm, Monofilament diameter: 70 μm, Threads/cm: 55, Open area: 33%, Type: Plain weave mesh).

Other suitable substrates for the fabric or other weave of the inner and/or outer substrate layer exist that have satisfactory biocompatibility and can be chemically modified so that the disclosed layer-by-layer production method can be used. Examples of suitable substrates include, but are not limited to, the substrates shown in Table 1.

TABLE 1

| Material | Structure |
|---|---|
| 2-Hydroxyethyl methacrylate (HEMA) | 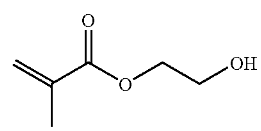 |
| 2-Phenylethyl methacrylate (PEM) | 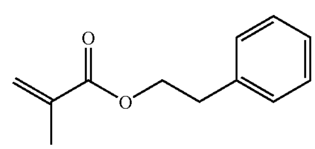 |
| Polyethylene glycol (PEG) | 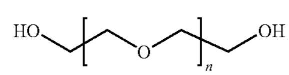 |
| Methyl methacrylate (MMA) | 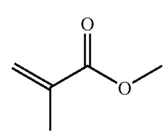 |
| Polydimethylsiloxane (PDMS) macromer | 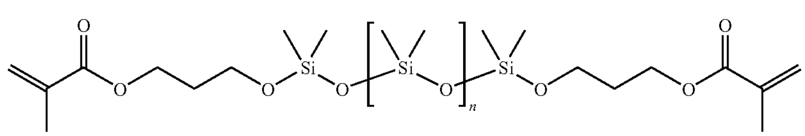 |
| Polyvinyl alcohol (PVA) hydrogel | 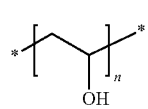 |

In the rigid epiretinal or subretinal implants, the substrate is a suitable rigid structure such as, but not limited to, a pin made of platinum or titanium.

Preparation of the Substrate Layers

Attaching bacteriorhodopsin to the inner substrate layer is a critical requirement for making the retinal ion patch. Several designs provide good adhesion while maintaining flexibility and ion motion. In certain embodiments, DACRON microfibers are used. DACRON has a relatively low glass transition temperature (GTT) of 75° C. coupled with a high melting temperature of 260° C. This combination allows gold sputtering onto the DACRON surface of a sample at 80° C., above the GTT but well below the melting point. The result is excellent adhesion of the gold on the surface without deforming or damaging the integrity of the fabric. Gold-binding bacteriorhodopsin mutants can then covalently bond to the gold layer, and then subsequent bacteriorhodopsin layers may be added via the layer-by-layer (LBL) method (FIG. 2A).

In an alternative embodiment, the DACRON surface may be modified by reduction of the surface carbonyl functional groups to render a negative surface charge (Phaneuf et al., 1995, J. Applied Biomat. 6:289-99). In one embodiment of these methods, the fabric is washed in a scouring solution (10 g $Na_2CO_3$, 10 mL TWEEN 20, 1 L dd$H_2O$) for 30 minutes at 60° C. The fiber is then washed in dd$H_2O$ for 30 minutes at 60° C. before a mild hydrolysis with a 0.5% (w v-1) NaOH for 30 minutes at 100° C. Next, the fiber is rinsed with dd$H_2O$ at ambient temperature and is then ready for LBL addition (FIG. 2B). The advantage of this method is simplicity and improved ion transport through the back of the fabric. A possible slight disadvantage is a decrease in the reflectivity of the surface, but the use of close-weave white microfiber provides adequate reflectivity.

The Protein Film of the Artificial Retinal Implants

Native Bacteriorhodopsin

Bacteriorhodopsin is a transmembrane protein found in the cell membrane of halobacteria such as *Halobacterium salinarum*, an archaea native to hypersaline environments. Bacteriorhodopsin exhibits unique photophysical properties that enable the protein to be used in photonic and biophotonic devices. When dissolved oxygen concentrations drop below levels sufficient for respirative oxidative phosphorylation, bacteriorhodopsin is expressed by *H. salinarum* to produce the purple membrane. The purple membrane is comprised of a semicrystalline matrix of bacteriorhodopsin trimers, which form the quaternary structure of bacteriorhodopsin, and allows the organism to efficiently undergo photosynthesis as a means of energy production under oxygen limiting conditions. The large surface area exhibited by the purple membrane, typically over 50% of the total membrane area, produces a significant pH gradient across the extracellular and intracellular membrane surface. Thus, "purple membrane" is used herein when macromolecular manipulation of the protein is conducted and "bacteriorhodopsin" is used when manipulation of the monomeric structure is performed.

The wild-type sequence of bacteriorhodopsin from *H. salinarum* is as follows:

(SEQ ID NO: 2)
MLELLPTAVEGVSQAQITGRPEWIWLALGTALMGLGTLYFLVKGMGVSDP

DAKKFYAITTLVPAIAFTMYLSMLLGYGLTMVPFGGEQNPIYWARYADWL

FTTPLLLLDLALLVDADQGTILALVGADGIMIGTGLVGALTKVYSYRFVW

WAISTAAMLYILYVLFFGFTSKAESMRPEVASTFKVLRNVTVVLWSAYPV

VWLIGSEGAGIVPLNIETLLFMVLDVSAKVGFGLILLRSRAIFGEAEAPE

PSAGDGAAATSD.

Figure 5:
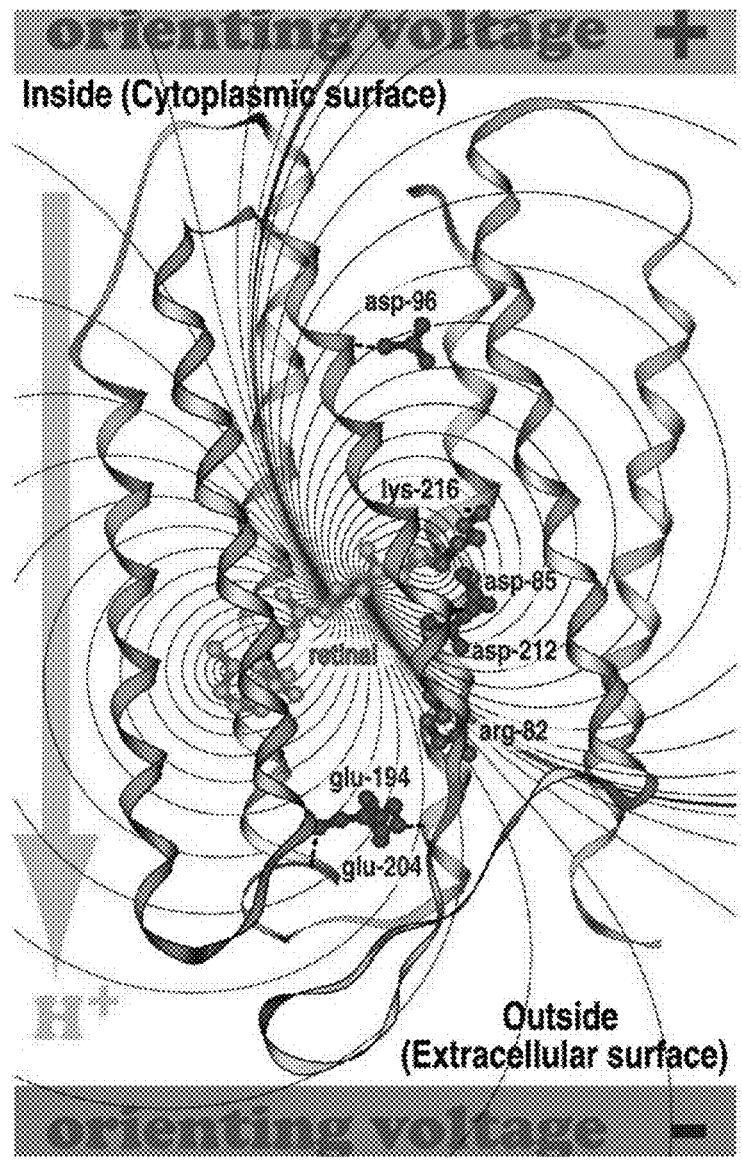
FIG. 5 shows schematic diagrams of bacteriorhodopsin. Panel A is a schematic diagram showing the three-dimensional structure of bacteriorhodopsin, including the key residues, helical segments, and proton pumping direction of the protein with respect to electrophoretic orientation. Panel B shows the amino acid sequence (SEQ ID NO:1) and secondary structure of bacteriorhodopsin.
Figure 5:
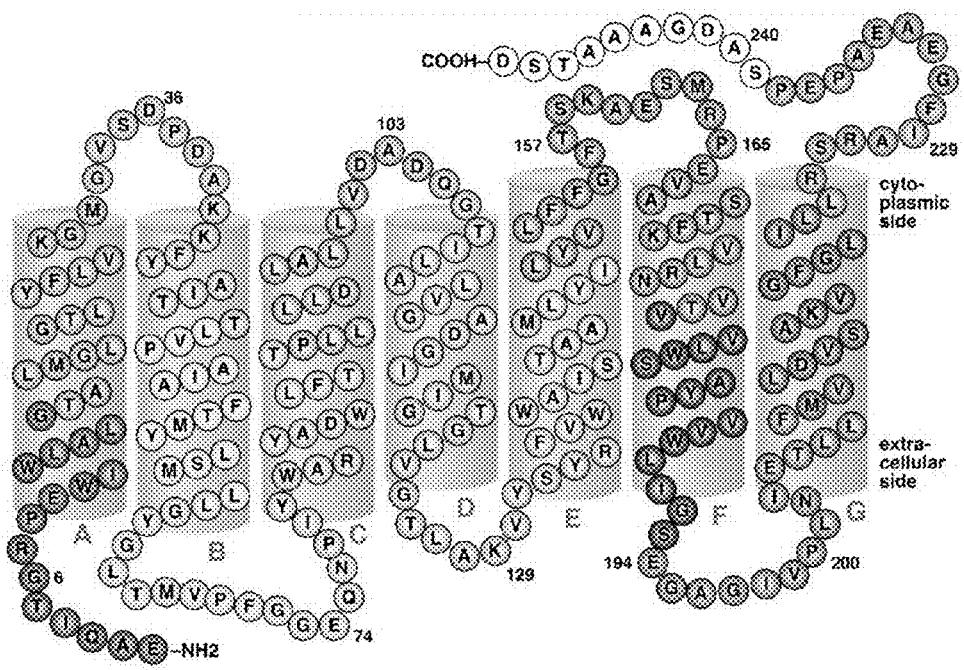
Figure 6:
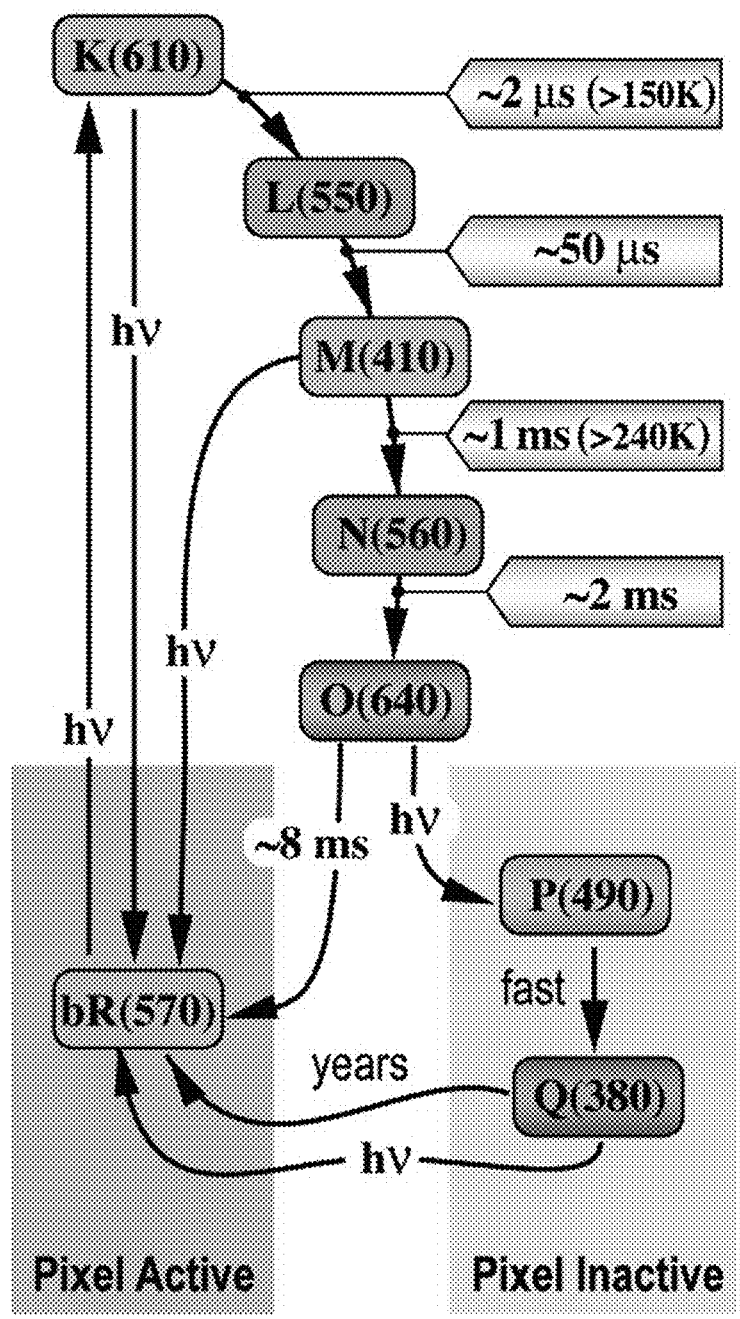
FIG. 6 is a schematic showing the photocycle of bacteriorhodopsin.

The secondary structure of bacteriorhodopsin consists of seven transmembrane α-helices oriented around an organic chromophore (FIG. 5). The light absorbing chromophore is all-trans retinal (polyene carbon atoms are shown as light grey in the center of FIG. 5A), which is covalently bound to Lys-216 in Helix VII via a protonated Schiff base linkage. A complex photochemical cycle, approximately 15 ms in duration, is initiated when a photon is absorbed by the chromophore in the light-activated resting state (bR) (FIG. 6). This photocycle transports a proton from the intracellular to the extracellular side of the purple membrane, creating the aforementioned pH gradient that drives ATP-synthase to chemiosmotically synthesize ATP. This process occurs every time a photon is absorbed by the photochemically stable retinal moiety. Site directed mutagenesis has been used to explore the effect of decreasing photocycle time on the ion flux.

Photochemical stability is quantified as the number of times a photochromic material can be photoconverted between two species before 37% (l/e) of the irradiated ensemble denatures. This number is called the cyclicity, and it exceeds $10^6$ for bacteriorhodopsin at ambient temperature. Few organic photochromic materials approach this value, and those that have high cyclicities typically have low quantum efficiencies for photoconversion. The high cyclicity of bacteriorhodopsin is due to the protective features of the integral membrane protein and semicrystalline purple membrane structure, which serves to isolate the chromophore from reactive oxygen, singlet oxygen, and free radical species. These photonic properties make bacteriorhodopsin an excellent candidate for application in many bioelectronic and biophotonic devices that include: random access thin film memories, neural-type logic gates, photon counters and photovoltaic converters, reversible holographic media, artificial retinas, picosecond photodetectors, spatial light modulators, associative memories, two-photon volumetric memories, pattern recognition systems, real-time holographic imaging systems, and branched-photocycle volumetric memories. Key to this application is the excellent stability of this protein. Nature has designed bacteriorhodopsin to function at the high temperatures experienced in salt marshes, and to operate over a large range of pH and light flux. Thus, bacteriorhodopsin is an excellent choice as the photoactive component for artificial retinas.

FIGS. 5A and 6 show diagrams representing the proton pumping process and the photocycle of bacteriorhodopsin, respectively. When bacteriorhodopsin absorbs light, the protein undergoes conformational changes that are relayed as spectrally discrete photointermediate states constituting a photocycle. The absorption maximum of the M state in the bacteriorhodopsin photocycle is considerably blue-shifted, whereas that of the O state is red-shifted relative to the resting state of native bacteriorhodopsin. Exposing the O state to red light leads into the branched photocycle.

The branched photocycle in wild-type bacteriorhodopsin occurs as a branch-off reaction via a sequential two-photon process from the O-state (FIG. 6). This alternate pathway is characterized by the short-lived P-state and a long-lived Q state that is stable for up to twelve years (Gillespie et al., 2002, J. Phys. Chem. B, 106:133352-61). The branched photochemistry of bacteriorhodopsin makes it possible to mediate the intensity of individual pixels of the artificial retina post-implantation by using sequential pulses of red light to convert a portion of the protein to the Q state. Formation of the Q state via the sequential two-photon process inactivates the pixel. Blue light of less than 450 nm in wavelength resets the pixel to activated status.

The hexagonal arrangement of bacteriorhodopsin in purple membrane patches provides the protein with extreme thermal and photochemical stability (although protein denaturation can occur at high temperatures and in severe chemical environments). The high cyclicity (i.e., the number of times the molecule can be photoactivated, which is greater than $10^8$) and quantum efficiency (0.65) of bacteriorhodopsin far exceeds that of any synthetic non-native photochromic material. The quantum efficiency represents the probability that an absorbed photon will generate a photocycle. Thus, each time the protein absorbs a photon of light, 65% of the time this process results in a complete photocycle (and the resulting signal). Interestingly, this is nearly identical to the efficiency of the retinal protein, rhodopsin. The intrinsic stability and sensitivity of bacteriorhodopsin are advantages of the artificial retinas described herein. While not wishing to be bound by estimates, it is estimated that the protein-based artificial retinas described herein could last at least eight years under normal light conditions, although artificial retinas having a shorter lifespan are also envisioned as part of the invention.

Implementation of bacteriorhodopsin as a source of light-induced ions requires that the protein be uniformly oriented over the entire multi-layered volume. The fabrication of bacteriorhodopsin thin films is well documented and a variety of methods exist with both advantages and disadvantages (See, e.g., Varo et al., 1983, Biophys. J. 43:47-51; Chen et al., 1991, Appl. Opt. 30:5188-96; He et al., 1998, Langmuir 14:1674-79; and Koyama et al., 1994, Science 265:762-65). Many of the methods, however, result in inadequate orientation of the protein for retinal implant applications. Alignment of the protein via a layer-by-layer (LBL) fashion, although laborious, allows for control of the film thickness and yields the most uniformly oriented films (He et al., 1999, Adv. Mater. 11:435-46). Methods for LBL assembly for use in the present methods for producing retinal implants are described below.

Bacteriorhodopsin Mutants

Bacteriorhodopsin Mutants with Enhanced Dipoles

The term "enhanced dipole mutant" (or simply, "dipole mutant") refers to any mutational substitution that involves a change in the overall charge of the protein that increases the intrinsic dipole moment of bacteriorhodopsin. Such mutations will provide a larger photochemical response in thin films by improving the packing density and orientation of the protein layers. A total of 8 single and 6 multiple enhanced dipole mutants have been generated which lead to improved performance. The best three single mutants are listed in Table 2.

TABLE 2

Photovoltaic Efficiency of Various Dipole Mutants

| | λ (nm) | Absorbance | Signal (mV) | PV efficiency | Normalized efficiency |
|---|---|---|---|---|---|
| Native | 570 | 1.2811 | 40 | 4.76 | — |
| E194K | 560 | 2.0145 | 75 | 8.53 | 1.79 |
| E9Q | 570 | 2.3145 | 100 | 11.13 | 2.34 |
| K159Q | 565 | 1.3574 | 280 | 28.18 | 5.92 |

The mutants listed in the table are described as X-#-Y, wherein X indicates the original amino acid (See FIG. 5B), # refers to the amino acid position, and Y indicates the amino acid present in the mutant. The reported values are from thin films prepared by electric field sedimentation (EFS) and normalized with respect to the native bacteriorhodopsin signal, yielding their total photovoltaic efficiency. This value standardizes the photovoltaic signal as a function of total protein in the film and the light output from the illuminating device. The equation used for photovoltaic efficiency is given by the equation 1:

$$\text{Efficiency} = \frac{\Delta V}{F \cdot N} \quad (1)$$

where $\Delta V$ is the measured photovoltaic response of the film (V), F is fraction of light absorbed by the sample at the wavelength of incident light, and N is the number of photons in the laser pulse (photons/pulse) as defined in equation 2, $$N = 5.03 \times 10^{12} \cdot E_{pulse} \cdot \lambda \quad (2)$$

where E is the energy output of the emitted light (mJ/pulse), and λ is the wavelength of emitted light (nm). The K159Q mutant yields an enhanced photovoltaic efficiency almost six times greater than the native protein. Thus, this mutant has been combined with other mutations to further enhance the photovoltaic efficiency of the protein. The ion pumping and photovoltaic efficiency scale proportionally, but photovoltaic measurements were used for comparative purposes because the latter are more easily measured in the laboratory. Examples of bacteriorhodopsin dipole mutants are shown in Tables 3 and 4.

TABLE 3

Examples of Bacteriorhodopsin Dipole/Q state Mutants

| No. | Mutation Present |
|---|---|
| 1. | E9Q |
| 2. | K159Q |
| 3. | E204Q |
| 4. | R164Q |
| 5. | A103D |
| 6. | K40Q |
| 7. | E74Q |
| 8. | G197K |
| 9. | E9Q/K40Q |
| 10. | E9Q/R164Q |
| 11. | E9Q/E74Q/K159Q |
| 12. | E9Q/K159Q/R164Q |
| 13. | E9Q/E74Q/K159Q/R164Q |

TABLE 4

Examples of Bacteriorhodopsin Enhanced Dipole Mutants

| No. | Mutation | Position | Charge |
|---|---|---|---|
| 1 | E9Q and E9N | Extracellular | Neutral |
| 2 | G33D and G33E | Intracellular | Negative |
| 3 | V34D and V34E | Intracellular | Negative |
| 4 | A39E and A39D | Intracellular | Negative |
| 5 | K40Q and K40N | Intracellular | Neutral |
| 6 | G72K and G72R | Extracellular | Positive |
| 7 | G73K and G73R | Extracellular | Positive |
| 8 | E74Q and E74N | Extracellular | Neutral |
| 9 | A103D and A103E | Intracellular | Negative |
| 10 | Q105E and Q105D | Intracellular | Negative |
| 11 | K159Q and K159N | Intracellular | Neutral |
| 12 | R164Q and R164N | Intracellular | Neutral |
| 13 | G195K and G195R | Extracellular | Positive |
| 14 | A196K and A196R | Extracellular | Positive |
| 15 | G197K and G197R | Extracellular | Positive |

TABLE 4-continued

Examples of Bacteriorhodopsin Enhanced Dipole Mutants

| No. | Mutation | Position | Charge |
|---|---|---|---|
| 16 | R227Q and R227N | Intracellular | Neutral |
| 17 | A233E and A233D | Intracellular | Negative |
| 18 | A240E and A240D | Intracellular | Negative |
| 19 | D241A and D241V | Intracellular | Neutral |
| 20 | G242K and G242R | Intracellular | Positive |
| 21 | A243E and A243D | Intracellular | Negative |
| 22 | A244E and A244D | Intracellular | Negative |
| 23 | A245E and A245D | Intracellular | Negative |

Plus all double, triple, quadruple, pentuple and sextuple combinations of above that, when combined, yield enhancement of the dipole moment (see text).

Bacteriorhodopsin Mutants with Altered Q State Formation

Genetically engineered mutants of bacteriorhodopsin with amino acid substitutions at positions V49X, T90X, D115X, E204X, E194X, L206X, D85X/D96X, T90X/V49X/E204X, where X can be any amino acid that is not the same as the amino acid being replaced, also display enhanced Q state formation.

The key advantage of these Q state mutants is the relative ease with which the protein can be converted into the Q state using relatively low-light excitation. When converting the bacteriorhodopsin Q state mutants to the inactive Q state via the sequential two-photon process, it is important that the short light pulses (less than one millisecond) are separated by about two milliseconds so that the first photon generates a photocycle and the second photon initiates the O(640)→P (490) photochemical transformation (See FIG. 6). The P(490) state quickly decays to form Q(380), and the protein is no longer active. The absorption spectrum of Q has a tail that extends into the visible spectrum; however, the Q state is not very photochemically active and will not convert back to the active bacteriorhodopsin state without a targeted blue pulse at about 410 nm. If all of the bacteriorhodopsin molecules associated with an individual pixel are converted to the Q state, the pixel is completely inactive. The bacteriorhodopsin Q state mutants described herein enhance the photochemical efficiency of converting bacteriorhodopsin to the inactive Q state by about 400 times relative to the native protein.

Examples of Q state mutants of bacteriorhodopsin are shown in Table 5. Bacteriorhodopsin mutants that display enhanced Q state formation can be combined with enhanced dipole mutants and may contain one or more of the mutant amino acid positions shown in Tables 3, 4, and 5. These multiple mutants also can be used in the bacteriorhodopsin films and artificial retinas described herein.

TABLE 5

Examples of Q State Forming Bacteriorhodopsin Mutants

| No. | Mutation |
|---|---|
| 1 | V49A[a] |
| 2 | V49N[a] |
| 3 | V49P[a] |
| 4 | V49F[a] |
| 5 | T90A |
| 6 | D85E[a] |
| 7 | R134I |
| 8 | R134A |
| 9 | E194A |
| 10 | E194N |
| 11 | E204Q |
| 12 | E204N |
| 13 | E204G |
| 14 | E204C |
| 15 | L206P |
| 16 | L206R |
| 17 | D85E/D96Q[a] |
| 18 | D85N/V49A[a] |
| 19 | T90A/V49A[a] |
| 20 | E194C/E204C |
| 21 | E194A/N202I |
| 22 | A196S/F208V |
| 23 | E204G/F208V |
| 24 | D212N/Y185F |
| 25 | I119T/T121S/A126T |
| 26 | T90A/V49A/E204Q[a] |
| 27 | A196S/I198L/P200T/E204A/T205Q/F208V |

[a]Bacteriorhodopsin mutants can enter the branched photocycle via a single photon process and/or a two photon process to form the permanent Q state. The remaining mutants form the Q state via a two photon process (sequential one photon reaction).

Fast Photocycle Bacteriorhodopsin Mutants.

Figure 7:
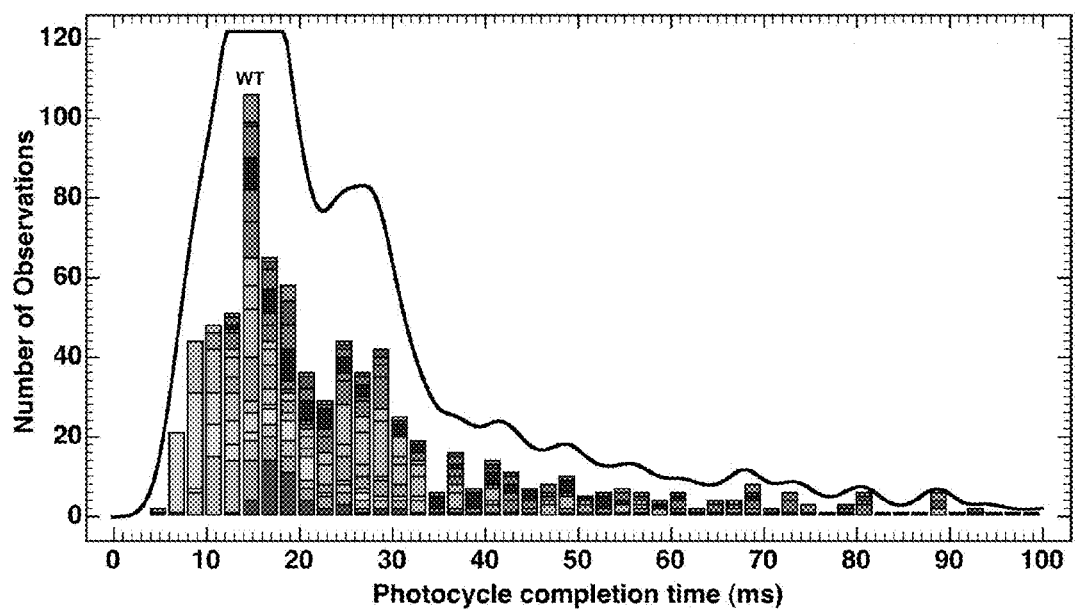
FIG. 7 is a graph showing the photocycle completion times of about 800 mutants of bacteriorhodopsin generated by semi-random mutagenesis in the segments marked in color. Most of the short photocycle mutants have a mutation in the B-C loop region shown in FIG. 5B.

To enhance the dynamic range of the bacteriorhodopsin protein layers, site directed mutagenesis was used to combine high dipole mutations with fast photocycle mutations. The latter mutants pump the ions more rapidly than the native protein, and thus can operate linearly under higher light intensities. The best mutants are shown in FIGS. 5B and 7, and the specific mutations are listed in Table 6.

TABLE 6

Bacteriorhodopsin Fast Photocycle Mutants

| Time (ms) | Mutation |
|---|---|
| 4.85 | S226C/I229R/F230L/G231S/A233P |
| 5.48 | Q75R |
| 5.94 | Q75L |
| 6.24 | E74V |
| 6.28 | L66I/G72S |
| 6.43 | N76K |
| 6.56 | M68L/Q75H |
| 6.66 | M68T/P70V |
| 6.70 | L66I |
| 6.71 | P70A |
| 6.71 | Q75M |
| 6.92 | S59T/L61V |
| 7.01 | Q75E |
| 7.05 | G72V |
| 7.09 | Q75H |
| 7.28 | F71V/G73V/Q75R |
| 7.42 | G63R |
| 7.53 | P70R/G72V/Q75H/N76H |
| 7.63 | F71Y/E74K |
| 14.87 | Native Protein (WT) |

Bacteriorhodopsin has a relatively efficient photocycle with a total photocycle time of about 15 ms at ambient temperature, which represents the total time necessary to repopulate 63% of the bR resting state. Using genetic engineering to shorten the photocycle allows for a retinal implant with a greater response linearity and bandwidth than one based on the native protein. This observation follows from the fact that a bright spot on the implant will saturate a protein ensemble much faster if it takes the protein 2-3 times longer to respond to light before returning to the resting state.

The fastest photocycle mutant, which involves a combination of five mutations, did not work when combined with the high dipole moment mutants. The next five all worked equally well when combined with K159Q, the best enhanced dipole mutant (data not shown).

Gold Binding Bacteriorhodopsin Mutants

In certain embodiments, the artificial retinas utilize a binder layer that comprises gold, which allows the bacteriorhodopsin protein layers to bind to the inner substrate. In such embodiments, gold-binding bacteriorhodopsin mutants are used to bind to the gold binder layer. The gold-binding mutants serve as the base scaffolding of the protein thin films and direct the orientation of subsequent protein layers. Native bacteriorhodopsin does not contain any cysteine residues, and thus cysteine residues are strategically introduced into these mutants in the loop regions of the protein. Such placement allows specific orientation of the protein and control of the photochemical polarity. The cysteine thiol group reacts with the gold atoms to covalently attach the protein to the substrate surface. A library of twenty-four cysteine mutants are shown in Table 7. Cysteine residues are introduced at sites within the protein loop regions, which are identified using the published 3-D crystal structure of the protein (i.e., the 1C3W structure from the Protein Data Base). Only one cysteine atom per protein is required for gold binding, but bacteriorhodopsin mutants with two or three cysteine residue replacements also were created and tested.

TABLE 7

Targeted Gold-Binding Bacteriorhodopsin Mutants

| Mutant | Region | Side* |
|---|---|---|
| T5C | N terminus | Ex |
| G6C | N terminus | Ex |
| R7C | N terminus | Ex |
| E9C | N terminus | Ex |
| G33C | AB loop | Int |
| V34C | AB loop | Int |
| S35C | AB loop | Int |
| D36C | AB loop | Int |
| A39C | AB loop | Int |
| K40C | AB loop | Int |
| G72C | BC loop | Ex |
| G73C | BC loop | Ex |
| E74C | BC loop | Ex |
| Q75C | BC loop | Ex |
| A103C | CD loop | Int |
| Q105C | CD loop | Int |
| K129C | DE loop | Ex |
| V130C | DE loop | Ex |
| Y131C | DE loop | Ex |
| S132C | DE loop | Ex |
| K159C | EF loop | Int |
| E161C | EF loop | Int |
| S162C | EF loop | Int |
| R164C | EF loop | Int |
| E166C | EF loop | Int |
| G195C | FG loop | Ex |
| A196C | FG loop | Ex |
| G197C | FG loop | Ex |
| I198C | FG loop | Ex |
| P200C | FG loop | Ex |
| N202C | FG loop | Ex |
| E204C | FG loop | Ex |
| R227C | C terminus | Int |
| G231C | C terminus | Int |
| A233C | C terminus | Int |
| A240C | C terminus | Int |
| A241C | C terminus | Int |
| A242C | C terminus | Int |

*Ex indicates that the extracellular surface is bound to gold, and Int indicates that the intracellular surface is bound to gold.

Typically, about two to about five layers of gold-binding bacteriorhodopsin mutants are first deposited onto the gold layer, followed by the native bacteriorhodopsin, enhanced dipole mutants, fast photocycle mutants, chloride pump mutants, ion pump mutants, or combinations thereof, that have had their surface charges modified to accommodate the use of the electrostatic layer-by-layer technique for production of bacteriorhodopsin films as described below. In certain embodiments, about three layers of gold-binding bacteriorhodopsin mutants are first deposited onto the gold layer, followed by native bacteriorhodopsin, enhanced dipole mutants, fast photocycle mutants, chloride pump mutants, ion pump mutants, or combinations thereof.

Chloride Pumping Mutants

Artificial retinas can be designed using halorhodopsin, however, this protein is not stable enough for long-term use in a retinal implant. This stability problem has been solved by genetically engineering bacteriorhodopsin to pump chloride ions (Cl$^-$) while maintaining the bacteriorhodopsin semicrystalline lattice, which is a major source of the stability of bacteriorhodopsin.

The primary mutation that converts bacteriorhodopsin to a Cl$^-$ pump is D85T, which introduces a hydroxyl functional group into the protein (Sasaki et al., 1995, Science 269:73-75; Paula et al., 2001, Biophys. J. 80:2386-95). Speculation has been made that this functional group temporarily binds the Cl$^-$, initiating the uptake step of the ion (Essen, 2002, Curr. Opin. Struct. Biol. 12:516-22). To increase efficiency, larger residues (e.g., Asn, Phe, and Tyr) in the extracellular loop regions may be replaced with smaller residues (e.g., Ala, Val, and Gly) using site directed mutagenesis.

Figure 8:
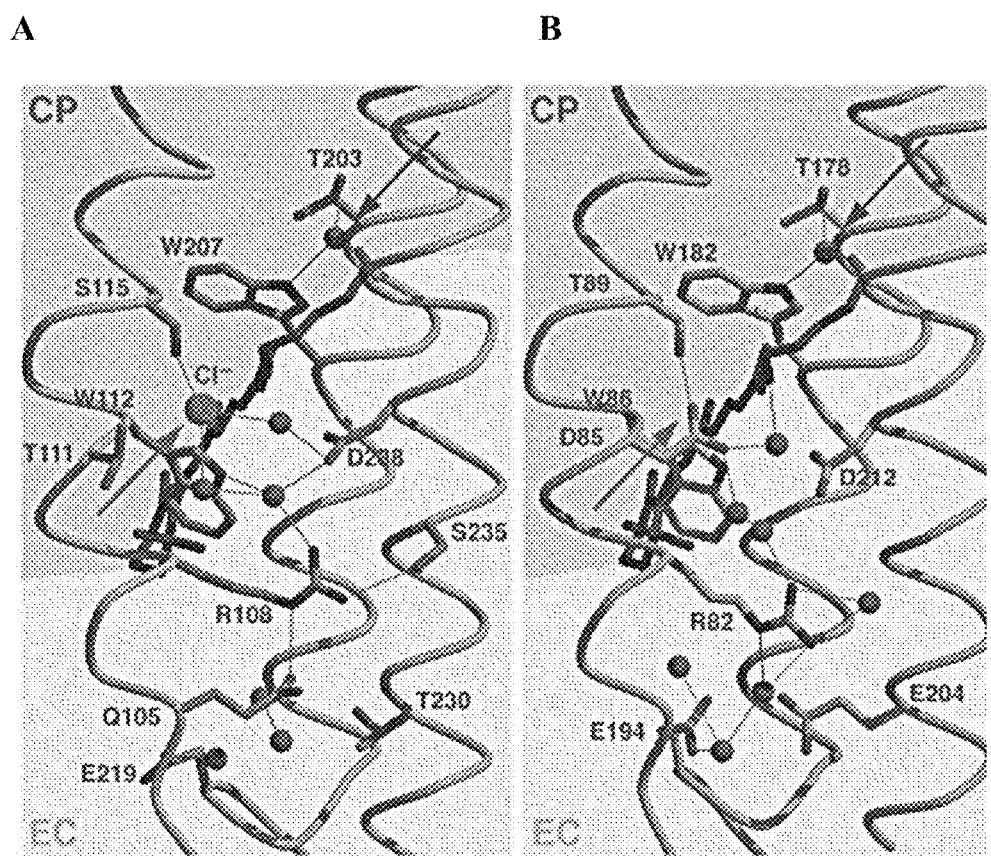
FIG. 8 shows schematic diagrams of portions of the three dimensional structure of halorhodopsin and a bacteriorhodopsin chloride pump mutant. Panel A shows where the initial uptake of the chloride ion occurs in halorhodopsin. Panel B shows the region of a bacteriorhodopsin chloride mutant in which the mutations are introduced to allow bacteriorhodopsin to act as a chloride pump. In particular, the aspartic acid residue at position 85 of this mutant is substituted with a threonine residue. In addition, for efficiency, larger residues in the extracellular loop regions may be replaced with smaller residues using site directed mutagenesis.

During the phototransduction of Cl$^-$, the D85T mutant forms an intermediate in which the Cl$^-$ induces the transient deprotonation of the glutamate residue at position 204 of the bacteriorhodopsin mutant. FIG. 8 shows three dimensional structures of halorhodopsin and bacteriorhodopsin, depicting where the chloride ion binds the protein. Halorhodopsin does not undergo any such deprotonation of the homologous residue, which is a neutral threonine ion (Essen, 2002, Cur. Opin. Struct. Biol. 12:516-22). The change in the protonation state may be instrumental in the photocycle of the D85T mutant, and mutations to the glutamate residue at position 204 of the bacteriorhodopsin mutant may inhibit or halt the phototransduction of all ions. The E204T mutant, however, increases the homology of bacteriorhodopsin to halorhodopsin and provides improved throughput.

The Differential Signal of the Bacteriorhodopsin Films

The optic nerve must transfer a large amount of information to the brain. To improve the efficiency of this process, the signal generated by photoreceptors upon absorption of light is mediated by the bipolar and ganglion network so that the signals sent along the optic nerve are edge-enhanced and differential. The thin bacteriorhodopsin film of the rigid artificial retinal implants described herein can provide differential responsivity (Chen, Z., and Birge, R. R. (1993), "Protein based artificial retinas," Trends Biotech. 11, 292-300). The basic elements of a differential signal are: (1) an initial signal upon absorption of light by bacteriorhodopsin, followed by (2) a period of no signal, and ultimately (3) a negative-going signal when the light is turned off.

Figure 9:
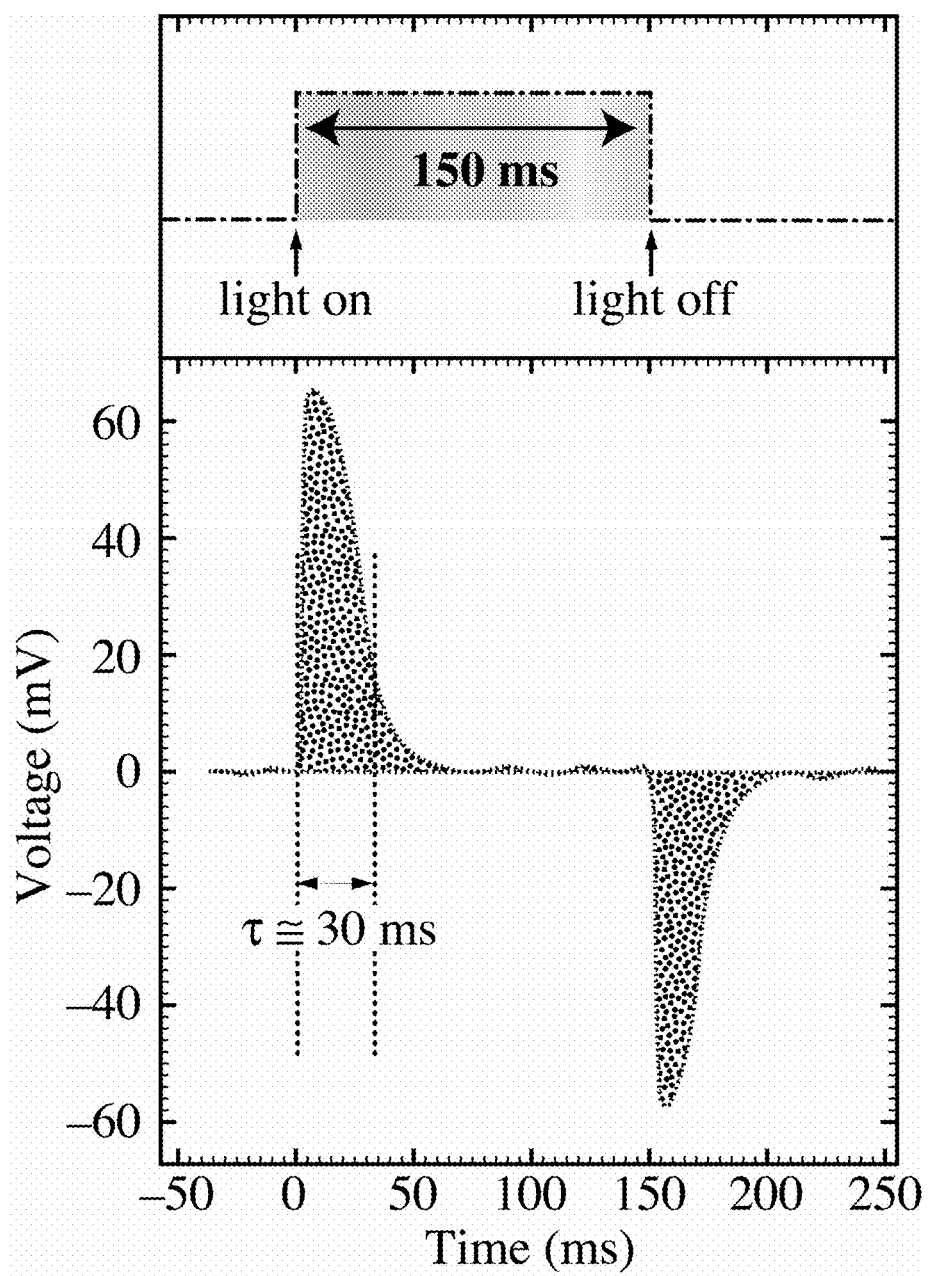
FIG. 9 is a graph showing the differential responsivity of the artificial retinal pixels of the rigid retinal implants.

FIG. 9 is a graph showing the differential responsivity of the rigid artificial retinal pixels. The size of the differential (reversed voltage) light-off signal (at time=150 milliseconds) is adjustable from 5% to 95% of the initial photovoltaic peak shown at 0 milliseconds by changing the interlayer polymer permeability. A differential signal has a higher probability of firing the bipolar or ganglion cells of the natural retina than does a constant signal that is on during the entire duration of the light stimulus. An extremely short pulse will not generate a differential signal because the source of the differential signal is a buildup of charge at the pixel that, upon backflush, generates the opposite (differential) signal. The existence and magnitude of the differential signal can be controlled by the nature of the polymer that is used in making the bacteriorhodopsin films using an electrostatic layer-by-layer method as described below.

Production of the Bacteriorhodopsin Films

A critical aspect of making the artificial retinas described herein is to provide an oriented protein film with the appropriate ionic gradient or photovoltaic properties. To provide optimal control over the properties of the film, the electrostatic layer-by-layer method can be used to produce the bacteriorhodopsin film described herein. This method uses a positively charged polymer between each protein layer.

Figure 10:
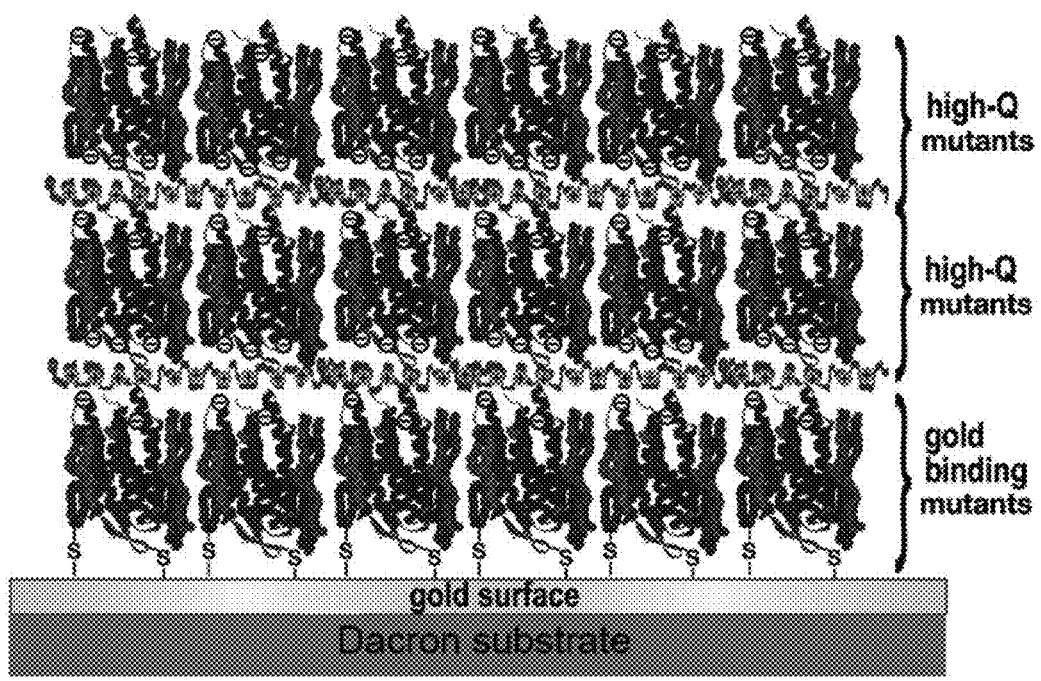
FIG. 10 is a schematic diagram showing the arrangement of layers of bacteriorhodopsin and the cationic polymer within one embodiment of the flexible artificial retinal implant (a row of "plus" signs enclosed within circles represents a layer of the positively-charged cationic polymer). In this embodiment, a DACRON microfiber is used as the inner substrate of the ion patch, and gold is the binder. This arrangement of layers also may be used in the rigid artificial retinal implant, in which the substrate may be a platinum or titanium pin.

FIG. 10 is a diagram showing the arrangement of protein and the cationic polymer poly(diallyldimethylammonium chloride) (PDAC). Other cationic polymers can be substituted for PDAC to mediate the size of the differential signal. Examples of cationic polymers that can be used to assemble the bacteriorhodopsin layers include, but are not limited to, those shown below in Table 8. Examples of Thin Film Intercalating Agents include, but are not limited to those shown below in Table 9 (See, e.g., Bromley et al. (2007) *Adv. Mater.* 19: 2433).

TABLE 8

Cationic Polymers for Layer-by-Layer Assembly of Bacteriorhodopsin Layers

| Polymer | CAS No. | Reference |
|---|---|---|
| Poly(diallyldimethylammonium chloride) ("PDAC") $(C_8-H_{16}-Cl-N)_n$ | 26062-79-3 | See, e.g., He et al. (1998) Langmuir 14: 1674 |
| 3-(1-Pyridinio)-1-propanesulfonate ("PPS") $(C_8-H_{11}-N-O_3-S)$ | 15471-17-7 | See, e.g., Zhang et al. (2003) Biophys. J. 84: 2052. |

TABLE 9

Thin Film Intercalating Agents

| Agent | CAS No. |
|---|---|
| 3-aminopropyltriethoxysilane3-aminopropyltriethoxysilane ("3-APTES") $(H_2N(CH_2)_3Si(OC2H5)_3)$ | 919-30-2 |
| Polyvinyl alcohol (89-98K MW) ("PVA") [—CH$_2$CHOH—] | 9002-89-5 |
| Poly-L-Lysine MW: 500-2000 g/mol | 25988-63-0 |

The intercalating agents are mixed with the cationic polymers in 20-50% by weight ratios to provide enhanced conductivity of the ions through the cationic polymer layer.

Although FIG. 10 shows only one layer of the bacteriorhodopsin gold binding mutant, use of at least about two to about five individual layers of bacteriorhodopsin gold binding mutant molecules provides a higher quality gold binding main layer prior to adding the critical layer(s) of native bacteriorhodopsin protein, dipole mutant, fast photocycle mutant, chloride pump mutant, ion pump mutant, or combination thereof. The individual layers of the bacteriorhodopsin gold binding mutant main layer are deposited on the thin gold layer deposited on the inner substrate layer of the subretinal implant, for example, using an automated apparatus as described herein.

Calibration of the Rigid Artificial Retina Post-Implantation

After implantation, each pixel is active and when the protein associated with that pixel absorbs light, it will generate a nerve impulse in the nerve into which the pin has been inserted. Some pins will miss nerve cells entirely, and they are effectively turned off for that reason. Other pins will intercept nerve cells which generate spurious signals either because the nerve cell is associated with a photoreceptor with a spatial position mutant to the nerve cell or the insertion process has involved multiple nerves which generate conflicting signals. The end result is that some pixels will need to be turned off for the patient to have spatially coherent vision. Turning off spurious pixels will decrease the resolution of the artificial retina, but enhance the quality of visual reception. The fact that this design makes that possible represents one of the key comparative advantages of the rigid artificial retinal implants described herein over the existing artificial retinas.

The Q-state mutants used to construct the bacteriorhodopsin films described herein allow conversion of bacteriorhodopsin from a proton pumping entity into a static entity that no longer absorbs light in the visible region. A bacteriorhodopsin protein multilayer that has been converted to the Q-state will have an absorption maximum at ~380 nm, outside the normal visual range.

An imaging system (e.g., systems manufactured by Laser Diagnostic Technologies Inc. or Zeiss Meditec) can be modified to excite individual pixels of the artificial retina with a pulse of weak yellow light (590 nm). A patient who has received a rigid artificial retina is asked to identify the location of the excited pixel in reference to an inverted image of the back of the retina. This process can identify faulty pixels. The faulty pixels can be turned off using a 3 mJ pulsed of red light positioned by using the same optical framework that was used to image the artificial retina.

EXAMPLES

Example 1

Production of a Bacteriorhodopsin-Based Film for Retinal Implant

Implementation of bacteriorhodopsin as a source of light-induced ions requires that the protein be uniformly oriented over the entire multi-layered volume. The fabrication of bacteriorhodopsin thin films is well documented and a variety of methods exist with both advantages and disadvantages (See, e.g., Varo et al., 1983, Biophys. J. 43:47-51; Chen et al., 1991, Appl. Opt. 30:5188-96; He et al., 1998, Langmuir 14:1674-79; and Koyama et al., 1994, Science 265:762-65). Many of the methods, however, result in inadequate orientation of the protein for retinal implant applications. Alignment of the protein via a layer-by-layer (LBL) fashion, although laborious, allows for control of the film thickness and yields the most uniformly oriented films (He et al., 1999, Adv. Mater. 11:435-46).

Figure 11:
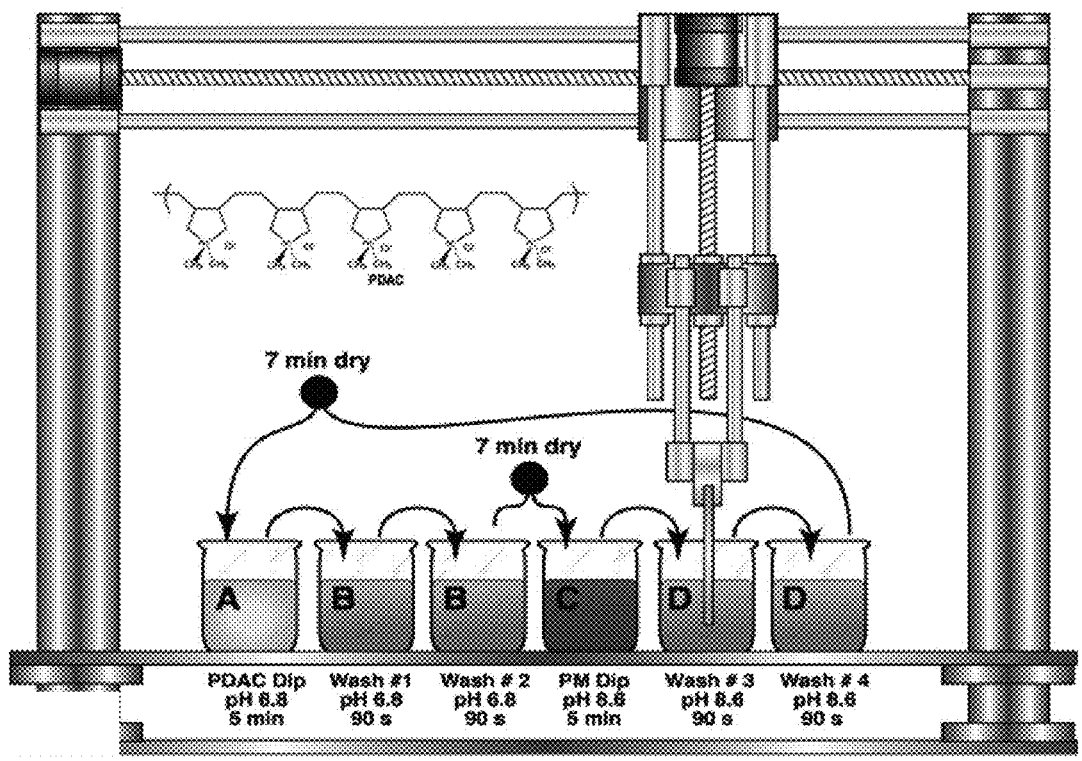
FIG. 11 is a schematic diagram showing an automated dipper apparatus that can be used to generate precision layers of bacteriorhodopsin during construction of the artificial retinal implant.

To increase the efficiency of the LBL method, an automated dipper system was constructed to move the thin film substrate through the multi-stage process (FIG. 11). Automation of the process eliminates human error and allows the process to be carried out in a clean room or laminar flow hood to minimize contamination. Automation also permits the formation of films with thicknesses requiring several days of consecutive dipping, a task too daunting to be performed by hand. The automated dipper was constructed from Thompson Industries linear slide arms and stepper motors. The motors are controlled by an RMV electronics control board ST-400NT, which comes packaged with a dynamic library written in C++. The subroutines and functions of this library were wrapped in an extended basic plugin and the compiled RealBasic program was used to call the necessary combination of functions to perform the dipping needed for thin film production. Furthermore, the present films uphold the direct relationship between film absorbance and number of protein layers described by He et al. (1998, J. Phys. Chem. B. 102: 7067-72).

FIG. 11 is a schematic diagram of the automated dipper used to generate precision layers of protein on the artificial retina. The gold film surface of the artificial retina is sequentially dipped into a series of beakers (or 50-ml conical tubes or other containers), each beaker containing the cationic polymer (e.g., PDAC), bacteriorhodopsin, or a wash buffer. Each complete cycle of dipping steps produces an individual bacteriorhodopsin layer on the substrate surface (e.g., DACRON). Multiple layers are produced by completing multiple rounds of the dipping cycle. For example, in FIG. 11, Beaker A contains the positively charged polymer PDAC, Beaker C contains the negatively charged bacteriorhodopsin, and the remaining beakers contain a series of wash buffers. The first few bacteriorhodopsin layers are generated using the gold-binding mutant in beaker C, after which the operator of the automated dipper is notified by the computer linked to the dipper to replace Beaker C containing the gold-binding mutant with Beaker C containing the high-Q mutant.

These methods provide significant control of the homogeneity and optical properties of the resultant protein films. In one embodiment, poly(diallyldimethyl ammonium chloride), or PDAC, was the organic cation used to bind the protein layers to each other (FIG. 10). Bacteriorhodopsin was prepared in an alkaline solution (50 mM Glycine, pH 9.5) to enhance the net negative charge of the molecule for adsorption. Each dip was followed by a series of water washes to prevent any loosely bound molecule from contaminating subsequent solutions. It was observed that 400 layers of oriented bacteriorhodopsin generates a single pass absorptivity of 0.88 units of optical density. When gold was used as the binder layer, the optimal configuration used about 400 layers because the gold layer reflects a majority of the light that has not been absorbed during the first pass. This embodiment allowed the 400 protein layers to absorb about 98% of the total light that reaches the protein film. A LBL film of native bacteriorhodopsin, composed of 200 protein layers on an ITO plate, exhibits a photovoltaic signal of 800 mV. Roughly twice this voltage is required to activate a rabbit retina and by analogy an adequate ion differential.

In general, about 200-400 layers of mutant bacteriorhodopsin provided an optimal optical density (0.88) because the thin gold film that is sputtered onto the substrate surface reflects most of the light that manages to pass through the protein film on the first pass (FIG. 10). The resulting protein films absorbed 98% or more of the light. Too many layers decrease the intensity of the signal. Too few layers also decrease the intensity of the signal by not absorbing a high enough fraction of the light.

Figure 12:
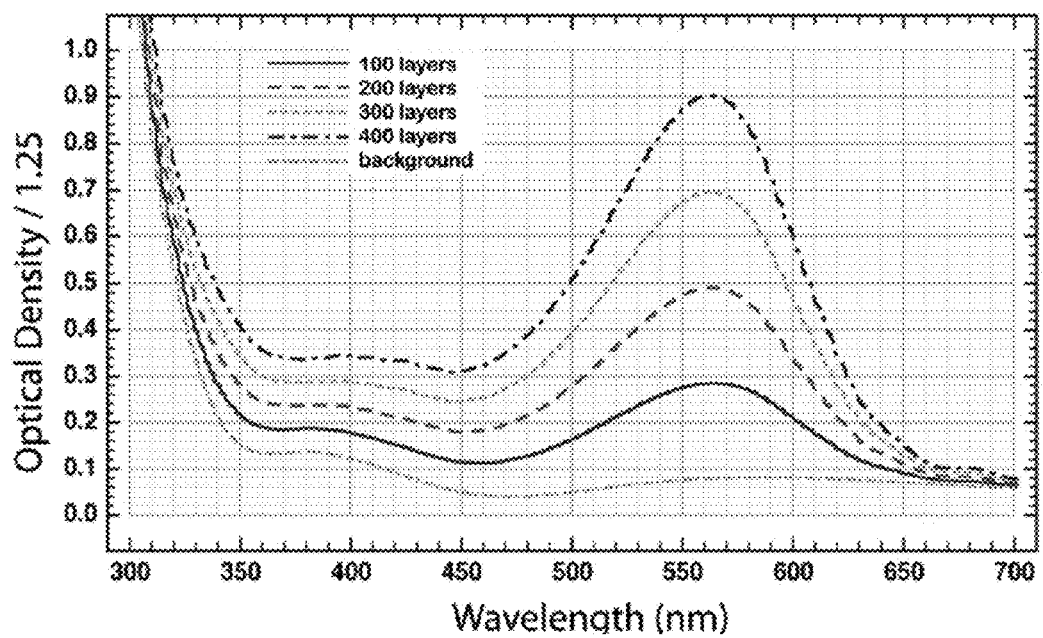
FIG. 12 is a graph showing the absorption spectra of the artificial retinal implant as a function of the number of bacteriorhodopsin layers deposited using the automated dipper apparatus. The horizontal axis is the wavelength measured in nanometers, and the vertical axis is the optical density or absorptivity (OD) divided by 1.25.

FIG. 12 is a graph of the absorption spectra of the artificial retina as a function of the number of protein layers deposited using the automated apparatus shown in FIG. 11. Note that the vertical axis is absorptivity (OD) divided by 1.25. The bacteriorhodopsin protein films described herein have an absorption maximum at 570 nm, closer to the human red cone than the wavelength of absorption of a human rod photoreceptor ($\lambda_{max}$=500 nm). Although bacteriorhodopsin can be genetically modified to provide a range of wavelengths in the visible spectrum, the nominal absorption maximum of the protein is at 570 nm, and this wavelength is the most easily achieved. Nevertheless, the protein absorbs efficiently from 420-630 nm, which provides an adequate wavelength range for an artificial retina.

As stated above, DACRON is the solid substrate used for some of the proposed flexible artificial retina designs. The material has already been demonstrated to be compatible with analogous LBL methods (See, e.g., Liu et al., 2005, Coll. Surf. B: Biointerfaces 46:117-26; Wyers et al., 1999, Cardiovasc. Pathol. 8:153-59; and Liu et al., 2007, J. Biomed. Mat. Res. 81A:692-704). Preparation of the DACRON fiber is accomplished in one of two scenarios. The first scenario sputters gold onto the fiber surface to create an electrically conductive material, to which gold-binding bacteriorhodopsin mutants can be covalently bound. Once the protein is covalently bound to the gold surface, the plate is rinsed with Milli-Q distilled water, and the gold plate is subjected to 2 cycles of LBL dipping with the same gold-binding bacteriorhodopsin mutant in beaker C. A new beaker containing a native bacteriorhodopsin, an enhanced dipole mutant, a fast photocycle mutant, a chloride pump mutant, an ion pump mutant, or a combination thereof, replaces beaker C for the subsequent number of dipper cycles. In an alternative scenario, preparation of the fiber requires a mild reduction of the surface carbonyl functional group to render a negative surface charge (Phaneuf et al. 1995, J. Applied Biomat. 6:289-99). In this scenario, gold and the gold-binding mutant are not used, and instead, the native bacteriorhodopsin, enhanced dipole mutant, fast photocycle mutant, chloride pump mutant, ion pump mutant, or combination thereof is in beaker C. In addition, other apparatuses, both automated and manual, also are contemplated for use in the layer-by-layer methods.

Example 2

Effect of Retinal Implant

A 55 year old patient having loss of vision caused by retinitis pigmentosa exhibits damaged or missing photoreceptor cells, but still has an active ganglion or bipolar neural network. A retinal implant as disclosed herein is implanted into the eye of the patient, replacing the damaged or missing photoreceptor cells. The retinal implant stimulates the nerve cells by inducing an ion gradient in the local medium or by inducing a photovoltaic signal, resulting in the increased vision of the patient.

In another embodiment, a 72 year old patient with macular degeneration has damaged photoreceptor cells but an active ganglion or bipolar neural network. A retinal implant as disclosed herein is implanted into the eye of the patient, replacing the damaged photoreceptor cells. The retinal implant stimulates the nerve cells by inducing an ion gradient in the local medium or by inducing a photovoltaic signal, resulting in the increased vision of the patient.

Incorporation by Reference and Other Embodiments

Throughout this application, various publications, patents, and/or patent applications are referenced in order to more fully describe the state of the art to which this composition and methods pertain. The disclosures of these publications, patents, and/or patent applications are herein incorporated by reference in their entireties to the same extent as if each independent publication, patent, and/or patent application was specifically and individually indicated to be incorporated by reference.

The invention illustratively described herein suitably may be practiced in the absence of any element or elements, limitation, or limitations not specifically disclosed herein. Thus, for example, in each instance herein any of the terms "comprising," "consisting essentially of," and "consisting of" may be replaced with either of the other two terms. The terms and expressions that have been employed are used as terms of description and not of limitation, and there is no intention that in the use of such terms and expressions of excluding any equivalents of the features shown and described or portions thereof, but it is recognized that various modifications are possible within the scope of the invention claimed.

It will be readily apparent to one skilled in the art that varying substitutions and modifications may be made to the invention disclosed herein without departing from the scope and spirit of the invention. For example, bacteriorhodopsins from *Halobacteria* species not listed herein fall within the scope of the present invention, as do bacteriorhodopsin mutants not specifically listed herein. Thus, such additional embodiments are within the scope of the present invention and the following claims.

---

What is claimed is:

1. A biocompatible ion permeable retinal implant, comprising at least one substrate layer and a bacteriorhodopsin film, wherein the bacteriorhodopsin film comprises a plurality of individual layers of a native bacteriorhodopsin or a bacteriorhodopsin mutant, wherein each individual layer of the native bacteriorhodopsin or bacteriorhodopsin mutant alternates with a layer of a cationic polymer, and wherein the bacteriorhodopsin mutant is selected from the group consisting of a chloride pump mutant, a dipole mutant, a photocycle mutant, a gold-binding mutant, an ion pump mutant, and a combination thereof.

2. The retinal implant of claim 1, wherein the retinal implant is flexible.

3. A biocompatible ion permeable retinal implant comprising a bacteriorhodopsin film, wherein the bacteriorhodopsin film is produced by a method comprising:
   a. modifying a substrate to produce a negative surface charge on the substrate, wherein the substrate is ion permeable;
   b. depositing a layer of a cationic polymer upon the modified substrate;
   c. depositing an individual layer of a native bacteriorhodopsin or bacteriorhodopsin mutant upon the layer of the cationic polymer, wherein the bacteriorhodopsin mutant is selected from the group consisting of a chloride pump mutant, a dipole mutant, a photocycle mutant, an ion pump mutant, and a combination thereof;
   d. depositing a layer of the cationic polymer upon the individual layer of the native bacteriorhodopsin or bacteriorhodopsin mutant;
   e. depositing additional alternating layers of the native bacteriorhodopsin or bacteriorhodopsin mutant and the cationic polymer as in steps (c) and (d) until about 200 to about 400 individual layers of the native bacteriorhodopsin or bacteriorhodopsin mutant have been deposited, thereby producing the bacteriorhodopsin film;

wherein the bacteriorhodopsin film further comprises a second substrate layer deposited upon the outermost layer of the bacteriorhodopsin film, and wherein the second substrate layer is ion permeable.

4. A retinal implant comprising a bacteriorhodopsin film wherein the bacteriorhodopsin film is produced by a method comprising:
   a. depositing a layer of gold upon a substrate;
   b. depositing an individual layer of a first bacteriorhodopsin mutant upon the gold, wherein the first bacteriorhodopsin mutant is a gold-binding mutant;

c. depositing a layer of a cationic polymer upon the individual layer of the gold-binding mutant of bacteriorhodopsin;

d. depositing additional alternating layers of the gold-binding mutant of bacteriorhodopsin and the cationic polymer as in steps (b) and (c) until about two to about five individual layers of the gold-binding mutant of bacteriorhodopsin are deposited to form a main layer of the gold-binding mutant of bacteriorhodopsin;

e. depositing a layer of the cationic polymer upon the last deposited layer of the gold-binding mutant of bacteriorhodopsin;

f. depositing an individual layer of a native bacteriorhodopsin or second bacteriorhodopsin mutant upon the layer of the cationic polymer, wherein the second bacteriorhodopsin mutant is selected from the group consisting of a chloride pump mutant, a dipole mutant, a photocycle mutant, an ion pump mutant, and a combination thereof;

g. depositing additional alternating layers of the native bacteriorhodopsin or second bacteriorhodopsin mutant and the cationic polymer as in steps (e) and (f) until about 200 to about 400 individual layers of the native bacteriorhodopsin or second bacteriorhodopsin mutant have been deposited to form a main layer of the native bacteriorhodopsin or second bacteriorhodopsin mutant, thereby producing the bacteriorhodopsin film;

wherein the bacteriorhodopsin film further comprises a second substrate layer deposited upon the outermost layer of the bacteriorhodopsin film, and wherein the second substrate layer is ion permeable.

5. The retinal implant of claim 3, wherein the second substrate layer comprises a substrate selected from the group consisting of polyethylene terephthalate (PET), 2-hydroxyethyl methacrylate (HEMA), 2-phenylethyl methacrylate (PEM), polyethylene glycol (PEG), methyl methacrylate (MMA), polydimethylsiloxane (PDMS) macromer, and polyvinyl alcohol (PVA) hydrogel.

6. The retinal implant of claim 4, wherein the second substrate layer comprises a substrate selected from the group consisting of polyethylene terephthalate (PET), 2-hydroxyethyl methacrylate (HEMA), 2-phenylethyl methacrylate (PEM), polyethylene glycol (PEG), methyl methacrylate (MMA), polydimethylsiloxane (PDMS) macromer, and polyvinyl alcohol (PVA) hydrogel.

7. A biocompatible ion permeable flexible retinal implant, comprising an inner substrate layer, a binder layer, an oriented film of bacteriorhodopsin protein layers, and an outer substrate layer, wherein the inner substrate layer and the outer substrate layer are ion permeable.

8. A biocompatible rigid retinal implant comprising a plurality of pixels, wherein each pixel comprises a bacteriorhodopsin film operatively associated with a platinum or titanium pin, wherein the plurality of pixels is configured so as to interface the platinum or titanium pins with a ganglion cell layer or a bipolar cell layer of a patient's retina when the retinal implant is implanted into the patient's retina.

9. The retinal implant of claim 7, wherein the bacteriorhodopsin film is deposited upon a layer of gold deposited upon the tops of platinum or titanium pins.

10. The retinal implant of claim 7, wherein the bacteriorhodopsin film is deposited upon a layer of gold deposited on a pad associated with a platinum or titanium pin, wherein each pixel comprises a gold covered pad contacting one of the platinum or titanium pins.

11. A method for treating a patient having loss of vision caused by loss of retinal photoreceptor cells, comprising implanting into an eye of the patient the retinal implant of claim 1, thereby treating the patient having loss of vision caused by loss of retinal photoreceptor cells.

12. The method of claim 11, wherein the retinal implant converts light into an ion gradient in the eye of the patient.

13. The method of claim 11, wherein the retinal implant converts light into a photovoltaic signal in the eye of the patient.

14. The retinal implant of claim 1, wherein the cationic polymer is a flexible fabric or weave.

* * * * *